United States Patent
Audeh et al.

(10) Patent No.: US 10,492,709 B2
(45) Date of Patent: Dec. 3, 2019

(54) MAGNETIC PROBES FOR IN VIVO CAPTURE AND DETECTION OF EXTRACELLULAR VESICLES

(71) Applicant: Verily Life Sciences LLC, Mountain View, CA (US)

(72) Inventors: Mark Audeh, San Jose, CA (US); Joshua Simon Klein, Mountain View, CA (US); Anthony M Giannetti, Mountain View, CA (US); Stephen Morton, Santa Clara, CA (US); James Michael Higbie, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 437 days.

(21) Appl. No.: 15/293,558

(22) Filed: Oct. 14, 2016

(65) Prior Publication Data

US 2017/0143233 A1 May 25, 2017

Related U.S. Application Data

(60) Provisional application No. 62/257,530, filed on Nov. 19, 2015.

(51) Int. Cl.
*A61B 5/145* (2006.01)
*A61B 5/05* (2006.01)
(Continued)

(52) U.S. Cl.
CPC .......... *A61B 5/0515* (2013.01); *A61B 5/0022* (2013.01); *A61B 5/0071* (2013.01);
(Continued)

(58) Field of Classification Search
CPC ... A61B 5/0515; A61B 5/0022; A61B 5/0071; A61B 5/14546; A61B 5/1455;
(Continued)

(56) References Cited

U.S. PATENT DOCUMENTS

| 4,106,488 A | 8/1978 | Gordon |
| 5,188,738 A | 2/1993 | Kaali |

(Continued)

FOREIGN PATENT DOCUMENTS

| WO | 2013030601 | 3/2013 |
| WO | 2013118029 A1 | 8/2013 |

(Continued)

OTHER PUBLICATIONS

Raposo et al., "EVs: Exosomes, microvesicles, and friends", JCB, vol. 200, No. 4, pp. 373-383, 2013.*

(Continued)

*Primary Examiner* — Eric F Winakur
(74) *Attorney, Agent, or Firm* — McDonnell Boehnen Hulbert & Berghoff LLP

(57) ABSTRACT

Body-mountable devices are provided to detect the presence or status of an analyte in subsurface vasculature of a body by detecting fluorescent reporters that are bound to instances of the analyte in the subsurface vasculature. Such devices further operate to exert an attractive magnetic force on magnetic nanoparticle-containing probes that are configured to bind to the analyte, thus concentrating the analyte proximate the devices by magnetically exerting attractive forces on such probes that are bound to instances of the analyte. The analyte can be an extracellular vesicle that is characteristic of a cancer, and a body-mountable device as described herein could be used to detect such extracellular vesicles in a portion of subsurface vasculature such that a presence or status of a tumor could be determined based on an amount, presence, or other detected property of the extracellular vesicle.

19 Claims, 6 Drawing Sheets

(51) Int. Cl.
- A61B 5/1455 (2006.01)
- A61B 5/00 (2006.01)
- A61K 49/00 (2006.01)

(52) U.S. Cl.
CPC ........ A61B 5/1455 (2013.01); A61B 5/14546 (2013.01); A61B 5/681 (2013.01); A61K 49/0058 (2013.01); A61K 49/0093 (2013.01); A61B 2562/0223 (2013.01); A61B 2562/0238 (2013.01)

(58) Field of Classification Search
CPC ............ A61B 5/681; A61B 2562/0223; A61B 2562/0238; A61B 5/145; A61B 5/14532; A61K 49/0058; A61K 49/0093; A61N 2/002

See application file for complete search history.

(56) References Cited

U.S. PATENT DOCUMENTS

| | | |
|---|---|---|
| 6,292,680 B1 | 9/2001 | Somogyi et al. |
| 6,326,160 B1 | 12/2001 | Dunn et al. |
| 7,214,190 B1 | 5/2007 | Wilson |
| 7,701,580 B2 | 4/2010 | Bassler et al. |
| 7,723,056 B1 | 5/2010 | Clarke et al. |
| 7,763,856 B2 | 7/2010 | Kiesel et al. |
| 7,817,254 B2 | 10/2010 | Hegyi et al. |
| 7,817,276 B2 | 10/2010 | Kiesel et al. |
| 7,844,314 B2 | 11/2010 | Al-Ali |
| 7,894,068 B2 | 2/2011 | Bassler et al. |
| 7,951,061 B2 | 5/2011 | Foreman et al. |
| 8,153,949 B2 | 4/2012 | Kiesel et al. |
| 8,323,188 B2 | 12/2012 | Tran |
| 8,344,731 B2 | 1/2013 | Lee |
| 8,368,396 B2 | 2/2013 | Ueda |
| 8,368,402 B2 | 2/2013 | Lee et al. |
| 8,409,415 B2 | 4/2013 | Liu et al. |
| 8,529,428 B2 | 9/2013 | Creighton |
| 8,569,044 B2 | 10/2013 | Hoon et al. |
| 8,624,592 B2 | 1/2014 | Lee |
| 2003/0165912 A1 | 9/2003 | Sorge et al. |
| 2004/0259270 A1 | 12/2004 | Wolf |
| 2005/0054907 A1 | 3/2005 | Page et al. |
| 2006/0238194 A1 | 10/2006 | Gleich |
| 2007/0243137 A1 | 10/2007 | Hainfeld |
| 2007/0255122 A1 | 11/2007 | Vol et al. |
| 2008/0154101 A1 | 6/2008 | Jain et al. |
| 2008/0177180 A1 | 7/2008 | Azhari et al. |
| 2009/0156932 A1 | 6/2009 | Zharov |
| 2009/0234225 A1 | 9/2009 | Martin et al. |
| 2009/0299127 A1 | 12/2009 | Rudolph et al. |
| 2010/0049010 A1 | 2/2010 | Goldreich |
| 2010/0072994 A1 | 3/2010 | Lee et al. |
| 2010/0149519 A1 | 6/2010 | Toofan |
| 2010/0204674 A1 | 8/2010 | Forbes et al. |
| 2010/0222657 A1 | 9/2010 | Ibey et al. |
| 2010/0256465 A1 | 10/2010 | Bernstein et al. |
| 2010/0264090 A1 | 10/2010 | Ellis et al. |
| 2011/0028803 A1 | 2/2011 | Ollmar |
| 2011/0117028 A1 | 5/2011 | Zharov |
| 2011/0125071 A1 | 5/2011 | Chisena et al. |
| 2011/0301633 A1 | 12/2011 | Muck et al. |
| 2012/0078068 A1 | 3/2012 | Ulmer |
| 2012/0255791 A1 | 10/2012 | Blangé et al. |
| 2012/0259154 A1 | 10/2012 | Hong et al. |
| 2012/0289764 A1 | 11/2012 | Murakami et al. |
| 2013/0006092 A1* | 1/2013 | Ferrans .............. A61K 41/0028 600/411 |
| 2013/0144134 A1 | 6/2013 | Lee et al. |
| 2013/0172728 A1 | 7/2013 | Gaitas |
| 2013/0253550 A1 | 9/2013 | Beisel et al. |
| 2013/0316355 A1 | 11/2013 | Dryga et al. |
| 2013/0342205 A1 | 12/2013 | Prado et al. |
| 2013/0344507 A1 | 12/2013 | Stilwell et al. |
| 2014/0005522 A1 | 1/2014 | Zurovcik |
| 2014/0021105 A1 | 1/2014 | Lee et al. |
| 2014/0170201 A1 | 6/2014 | Levy et al. |
| 2014/0378794 A1* | 12/2014 | Conrad ................. A61B 5/681 600/317 |
| 2015/0065821 A1 | 3/2015 | Conrad |
| 2015/0125398 A1* | 5/2015 | Assouline .............. A61B 5/055 424/9.32 |
| 2015/0238125 A1* | 8/2015 | Acosta ................. A61B 5/0071 600/310 |

FOREIGN PATENT DOCUMENTS

| | | |
|---|---|---|
| WO | 2013173235 | 11/2013 |
| WO | 2014079505 | 5/2014 |

OTHER PUBLICATIONS

Sakabe, U.Y., et al., "Rapid Response Activatable Molecular Probes for Intraoperative Optical Image-Guided Tumor Resection," Hepatology, vol. 56, No. 3, p. 1170-1173 (2012).

Warren, A.D., et al., "Point-of-care diagnostics for noncommunicable diseases using synthetic urinary biomarkers and paper microfluidics," PNAS, Vo. 111, No. 10, p. 3671-3676 (2014).

Warren, A.D., et al., "Disease Detection by Ultrasensitive Quantification of Microdosed Synthetic Urinary Biomarkers," Journal of the American Chemical Society, vol. 136, p. 13709-13714 (2014).

Goergen, C.J., et al., "In vivo fluorescence lifetime detection of an activatable probe in infarcted myocardium," Journal of Biomedical Optics, vol. 17(5), p. 056001-1-6, (2012).

Weissleder, R., et al., "In vivo imaging of tumors with protease-activated near infrared fluorescent probes," Nature Biotechnology, vol. 17, p. 375-378 (1999).

Tannock, I.F., et al., "Acid pH in Tumors and Its Potential for Therapeutic Exploitation," Cancer Research, vol. 49, p. 4373-4384, (1989).

Mallidi, Srivalleesha, et al., "Photoacoustic imaging in cancer detection, diagnosis, and treatment guidance," Trends Biotechnol., vol. 29(5), p. 213-221 (2011).

Condeelis, J., et al., "In Vivo Imaging in Cancer," Cold Spring Harb Perspect. Biol., vol. 2, p. 1-22 (2010).

Mehrmohammadi, M., et al., "Photoacoustic Imaging for Cancer Detection and Staging," Curr Mol Imaging, vol. 2 (1), p. 89-105 (2013).

Faltas, B., "Cornering metastases: therapeutic targeting of circulating tumor cells and stem cells," Frontiers in Oncology, vol. 2, Article 68, p. 1-7 (2012).

Stuker, F., "Fluorescence Molecular Tomography: Principles and Potential for Pharmaceutical Research," Pharmaceutics, vol. 3, p. 229-274 (2011).

Galanzha, E.I., "Circulating Tumor Cell Detection and Caputre by Photoacoustic Flow Cytometry in Vivo and ex Vivo," Cancers, vol. 5, p. 1691-1738 (2013).

Nima, Z.A., et al., "Circulating tumor cell identification by functionalized silver-gold nanorods with multicolor, super-anhanced Sers and photothermal resonances," Scientific Reports, vol. 4, 4752, p. 1-8 (2014).

Galanzha, E.I., et al., "In vivo magnetic enrichment and multiplex photoacoustic detection of circulating tumour cells," Nat. Nanotechnol., vol. 4 (12), p. 855-860 (2009).

Lin, K.Y., et al., Nanoparticles that Sense Thrombin Activity as Synthetic Urinary Biomarkers of Thrombosis, ACS Nano, vol. 7(10). p. 9001-9009 (2013).

Kwong G.A., "Mass-encoded synthetic biomarkers for multiplexed urinary monitoring of disease," Nature Biotechnology, vol. 31, No. 1, p. 63-71 (2013).

Danino, T., et al., "Programmable probiotics for detection of cancer in urine," Science Translational Medicine, vol. 7, Issue 289, p. 1-12 (2015).

International Searching Authority, International Search Report and Written Opinion for International Application No. PCT/US2014/054321 dated Dec. 17, 2014, 14 pages.

(56) References Cited

OTHER PUBLICATIONS

Beck, "The Beck Protocol a First Aid Kit of the Future" pp. 11-26 (2002).
Dr. Clark Information Center, "Zapping" http://www.drclark.net/products-devices-a-techniques/zapper-basics/zapping, accessed online Sep. 15, 2015, available online Oct. 8, 2012.
Dr. Hulda Clark Zapper "AutoZap 5-Ultimate Hulda Clark Zapper Design" http://www.frequencyrising.com/hulda-clark-zapper.htm, accessed online Sep. 15, 2015, available online Oct. 13, 2011.
RecoveryRx "Technology—RecoveryRx Pain Relief Therapy" http://www.recoveryrx.co/technology/, copyright 2013, accessed online Sep. 15, 2015.
Sam "Meet sam" http://samrecover.com/about-sam/, accessed online Sep. 15, 2015, available online Nov. 4, 2014.
Wuhan HNC Technology Co., Ltd. "Hypertension Health Care Product From China" http://whhnc8.en.made-in-china.com/product/vByEKRNPMpcF/China-Hypertension-Health-Care-Product-From-China.html, accessed online Sep. 15, 2015.
Sota "The Silver Pulser" http://www.sota.com/default.aspx?p. 556, copyright 2002-2015, accessed online Sep. 15, 2015.
Manuel Arruebo et al., "Antibody-Conjugated Nanoparticles for Biomedical Application," Journal of Nanomaterials, vol. 2009 (2009) Article ID 439389, 24 pages (available at http://dx.doi.org/10.1155/2009/439389).
Shao et al, "Magnetic nanoparticles for biomedical NMR-based diagnostics," Beilstein journal of Nanotechnology, 2010, 1, 142-154.
Liu et al, "Magnetic resonance monitoring of focused ultrasound/magnetic nanoparticle targeting delivery of therapeutic agents to the brain," PNAS Early Edition, 2010, pp. 1-6.
International Searching Authority, International Search Report and Written Opinion for International Application No. PCT/US2016/057287 dated Jan. 9, 2017.

\* cited by examiner

MAGNETIC PROBES FOR IN VIVO CAPTURE AND DETECTION OF EXTRACELLULAR VESICLES

CROSS-REFERENCE TO RELATED APPLICATION

This application claims the benefit of and incorporates by reference the content of U.S. Provisional Application No. 62/257,530, filed Nov. 19, 2015.

BACKGROUND

Unless otherwise indicated herein, the materials described in this section are not prior art to the claims in this application and are not admitted to be prior art by inclusion in this section.

Extracellular vesicles (EVs) are microscopic vesicles that are produced by cells and that may be present in blood, interstitial fluid, or some other environment of interest. An EV can include a variety of substances disposed within, on the surface of, or within a lipid bilayer that forms the exterior wall of the EV. The composition of the cytosol, proteins, or other contents within the wall of the EV and/or the composition of membrane proteins or other elements disposed within or on the outer surface of the wall of the EV can be related to the type of cell that produced the EV, properties of the cell that produced the EV, or other factors of the origin or history of the EV. EVs can be produced by a cell, enter the circulation, and be transported, in the blood, to other locations in the body. EVs can be isolated from a blood sample and used to determine whether cancer cells or other cell types of interest that can produce EVs are present in the body.

SUMMARY

Some embodiments of the present disclosure provide a body-mountable device including: (i) a magnetic flux source that, when mounted to an external body, can exert an attractive magnetic force on one or more magnetic nanoparticles of a probe in a portion of subsurface vasculature, wherein the exerted magnetic force is sufficient to collect the probe proximate the magnetic flux source; (ii) a sensor that includes a light emitter and a light detector; and (iii) a controller that is operably coupled to the sensor and that includes a computing device programmed to perform controller operations. The probe includes multiple binding sites that enable the probe to bind to multiple instances of an analyte. A fluorescent reporter is present in the portion of subsurface vasculature and selectively binds to the analyte. The controller operations include: (a) operating the light emitter to illuminate the portion of subsurface vasculature; (b) operating the light detector to detect light emitted from the fluorescent reporter in response to the illumination; and (c) detecting the analyte based on the detected light.

Some embodiments of the present disclosure provide a method that includes: (i) introducing a probe into a body, wherein the probe includes multiple binding sites that enable the probe to bind to multiple instances of an analyte; (ii) introducing a fluorescent reporter into the body, wherein the fluorescent reporter selectively binds to the analyte; and (iii) operating a body-mountable device. The body-mountable device includes: (1) a magnetic flux source; and (2) a sensor that includes a light emitter and a light detector. Operating the body-mountable device includes: (a) applying the magnetic flux source to exert an attractive magnetic force, on one or more magnetic nanoparticles of the probe in a portion of subsurface vasculature of the body, that is sufficient to collect the probe proximate the magnetic flux source; (b) operating the light emitter to illuminate the portion of subsurface vasculature; (c) operating the light detector to detect light emitted from the fluorescent reporter in response to the illumination; and (d) detecting the analyte based on the detected light.

These as well as other aspects, advantages, and alternatives, will become apparent to those of ordinary skill in the art by reading the following detailed description, with reference where appropriate to the accompanying drawings.

DETAILED DESCRIPTION

Figure 1A:
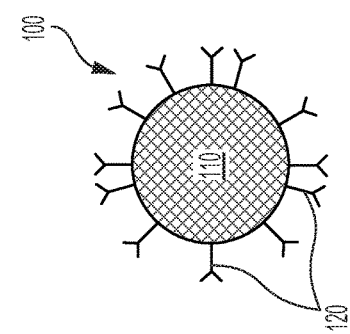
FIG. 1A is a schematic diagram of a probe configured to bind to an analyte, in accordance with an example embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

It can be beneficial to detect the presence, concentration, number, location, rate of occurrence, or other properties of analytes in the human body. Such analyte can be related to a health state of the body, and detection of such analytes can inform a course of treatment, the setting of a dosage of a drug, a dietary change, or some other actions related to the health of the body. For example, the detected analyte could include an extracellular vesicle (EV), a cancer cell, or some other substance related to the presence, status, or other properties of a cancerous tumor in a human body, and such information about the cancer could be determined based on the detected properties of the analyte. A course of treatment (e.g., a chemotherapeutic regimen, a surgical intervention) can be determined based on a detected presence, location, status (e.g., size, stage of cancer, type of cancer, degree or rate of metastasis), or other detected properties of the tumor. Other analytes, related to other health states of a body, could be detected.

In some examples, one or more fluorescent reporters or other contrast agents configured to bind to or otherwise selectively interact with an analyte could be introduced into a body to facilitate detection of the analyte. Such contrast agents could include fluorophores, dyes, Raman dyes, plasmonic nanoparticles, magnetic nanoparticles, fluorescent nanodiamonds, or other elements that can be detected from outside of a body, e.g., by optically interrogating a portion of subsurface vasculature that may contain such contrast agents. A detected presence, amount, degree of aggregation, fluorescence intensity, or other properties of such contrast agents in a body (e.g., in a portion of subsurface vasculature) could be used to determine information about the analyte (e.g., a presence or amount of the analyte in a body) and/or information about a health state related thereto (e.g., a presence or status of a tumor in a body).

However, detection of such contrast agents from outside of a human body (e.g., detection of fluorescent reporters within a portion of subsurface vasculature by a body-mountable device mounted to a skin surface proximate the portion of subsurface vasculature) can be difficult due to a variety of factors. For example, signals emitted from the contrast agents (e.g., fluorescence light, Raman-scattered light) could have a low intensity relative to other signals in the environment of the contrast agents (e.g., autofluorescence light from other elements of a human body, ambient light from outside the body). Further, an analyte of interest could have a low concentration and/or number in the body, could be infrequently generated/released, or could be otherwise difficult to detect in the body.

In order to facilitate detection of an analyte and/or of contrast agents bound thereto, the analyte could be collected and/or concentrated in the body. This could include introducing a probe into the body that is configured to bind to multiple instances of the analyte. Such binding can increase the signal detected from contrast agents (e.g., fluorescent reporters that are configured to selectively interact with the analyte) that are bound to the analyte by concentrating the analyte proximate to the probe. Further, the probe can act to maintain the bound analyte in the circulation (e.g., by preventing excretion via the kidneys and/or exiting the circulation into tissues of the body) and/or to collect the analyte over long periods of time, facilitating detection of the analyte (e.g., detection of the analyte in a portion of subsurface vasculature by a body-mountable device). Such a probe could include one or more magnetic nanoparticles (e.g., nanoparticles of superparamagnetic iron) to facilitate collection of the probe (and instances of an analyte bound thereto) proximate a sensor configured to detect the analyte and/or a fluorescent reporter or other contrast agent bound to the analyte (e.g., a sensor of a body-mountable device mounted to an external body surface proximate a portion of subsurface vasculature that may contain the probe and/or elements bound thereto).

Such a probe could be configured in a variety of ways to facilitate collection of an analyte in a portion of subsurface vasculature proximate a sensor. As noted above, individual instances of a probe could be configured to bind multiple instances of the analyte, e.g., by including multiple antibodies, aptamers, or other binding elements on the surface of the probe. The probe could include one or more magnetic elements (e.g., one or more magnetic nanoparticles) to facilitate collection of the probe (and instances of the analyte bound thereto) by exertion of attractive magnetic forces on the magnetic elements. The analyte-binding elements of the probe could be disposed on such magnetic elements and/or on a coating or other material containing or otherwise coupled to the magnetic elements. The probe could have a geometry, a hydrodynamic size, a mechanical compliance, or some other properties specified to maximize the amount or number of the analyte collected by the probe while allowing the probe to remain in circulation for a protracted period of time (e.g., days).

In some examples, the binding of the probe to an analyte could be nonspecific; that is, the probe could be configured bind to multiple different types of analyte. This could facilitate the collection and/or detection of multiple different types of, e.g., EVs. Conversely, fluorescent reporters that are configured to bind to the analyte (e.g., to instances of the analyte that have been collected by a probe) could be configured to bind to a specific type of analyte, facilitating detection of the specific type of analyte. Alternatively, the probe and fluorescent probe could both be configured to bind to a specific type of analyte to increase the specificity of detection of the specific analyte. This could include the probe and fluorescent reporter including respective different binding agents (e.g., respective different antibodies) that are both configured to selectively interact with the specific analyte.

The introduction into a body (e.g., into the vasculature of a body) of analyte-collecting probes and fluorescent reporters as described herein could be performed at different points in time. For example, the probe could be introduced a specified period of time (e.g., hours, days, weeks) before the introduction of a fluorescent reporter and/or detection of such a reporter in order to allow the probe to collect multiple instances of the analyte over the specified period of time. A fluorescent reporter or other contrast agent could have a limited lifetime in the body (e.g., could be degraded by the environment within the circulation and/or could be removed from the circulation by the kidneys) such that the fluorescent reporter can be introduced at multiple different points in time to provide for detection of the analyte at the multiple different points in time. Further, different fluorescent reporters that are configured to bind to respective different analytes could be introduced at respective different points in time, facilitating detection of the respective different analytes.

Those of skill in the art will understand a "probe" or a "fluorescent reporter" in their broadest sense and that they may take the form of any fabricated material, a molecule, cryptophane, a virus, a phage, etc. or some combination thereof. In practice, a plurality of probes and/or fluorescent reporters will be administered to a body, and one or more of the administered probes and/or fluorescent reporters can then be detected, in a portion of subsurface vasculature, by a body-mountable device mounted proximate the portion of subsurface vasculature or by some other device disposed on or within the body. The fluorescent reporter can include one or more optically detectable elements, e.g., fluorophores, Raman dyes, dyes, quantum dots, fluorescent nanodiamonds, or other elements that can be detected by optical methods. In some examples, the probe may also include such optically detectable elements and/or may be detectable by some other means (e.g., by magnetic detection of magnetic nanoparticle(s) of the probe). The probe and/or fluorescent reporter can be configured to selectively bind to one or more analytes (e.g., EVs, chemicals, hormones, peptides, DNA or RNA fragments, cells), for instance, to bind to a specific type of EV or to bind to multiple different types of EVs.

In some examples, the fluorescent reporters may be replaced by reporters designed to facilitate additional or alternative detection modalities. Plasmonic nanoparticles onto which are disposed Raman-active dyes could be used to provide a reporter having narrower excitation and/or emission lines and/or distinct spectral fingerprints for multiplex detection. In another example, highly optically absorbent particles such as radiation-damaged nanodiamonds or gold nanorods could be used as photoacoustic labels. In yet a further example, substances having large two-photon cross sections and narrow linewidths, such as nanodiamonds that include silicon-vacancy color centers or encapsulated two-photon dyes, could facilitate detection via two-photon excitation, providing for detection of such substances at greater depth within a tissue (e., at greater depths beneath a skin surface).

It should be understood that the above embodiments, and other embodiments described herein, are provided for explanatory purposes, and are not intended to be limiting.

Further, the term "tumor" as used herein should be understood broadly to include any mass of abnormal tissue growth within a body, e.g., a neoplasm. A tumor as described herein could be a benign tumor or a malignant tumor. A tumor could be a primary tumor (e.g., a mass of cells at the anatomical site of an original tumor cell) or a secondary tumor (e.g., a mass of cells grown from one or more cells that metastasized from an original tumor. A tumor could be formed from brain cancer cells, breast cancer cells, skin cancer cells, colon cancer cells, esophageal cancer cells, pancreatic cancer cells, or some other type of cancer cells. Accordingly, the probe and/or fluorescent reporter may be configured to bind to an EV, a cancer cell, an antibody, a cell membrane protein or other cell membrane element, or some other analyte or portion of an analyte that is produced by, emitted from, or otherwise indicative of the presence or status of a tumor.

II. Example Detection of Analytes Using Magnetic Nanoparticle Probes

As noted above, a probe may be introduced into the vasculature of a body (e.g., by intravenous injection) to collect an analyte of interest and to facilitate detection of such an analyte (e.g., by detecting a fluorescent reporter or other contrast agent bound to the analyte) in the body. This can include magnetically collecting the probe (and any instances of the analyte bound thereto) in a portion of subsurface vasculature by exerting an attractive magnetic force on the probe. The probe can be configured to bind multiple instances of the analyte, facilitating detection of the analyte directly (e.g., by optically interrogating a fluorophore of the analyte) and/or indirectly by detecting a fluorescent reporter or other contrast agent bound to the analyte. Binding to such a probe can additionally prevent bound instances of the analyte from leaving the circulation, e.g., by exiting the circulation into tissue, by being filtered by the kidneys, or by some other process.

The probe could be collected in a portion of subsurface vasculature proximate to a sensor, and the sensor could be operated to detect instances of the analyte bound to the probe and/or to detect a fluorescent reporter bound to instances of the analyte. The sensor could be part of a body-mountable device (e.g., a handheld device, a desktop device, or some other device configured to be mounted to an external body surface proximate to a portion of subsurface vasculature) that also includes a magnetic flux source or other elements configured to exert an attractive magnetic force on the probe that is sufficient to collect the probe proximate to the sensor.

The probe could be introduced into a body and could, over a period of time, collect multiple instances of an analyte by binding to the analyte. The probe could be collected (e.g., by exerting an attractive magnetic force) and a fluorescent reporter (or other contrast agent) that is configured to selectively bind to the analyte could also be introduced to facilitate detection of the analyte that is bound to the probe FIG. 1A shows a schematic of an example probe 100. The probe 100 includes a central core 110 on which a plurality of binding agents 120 are disposed. The core 110 includes one or more magnetic nanoparticles to which magnetic forces can be applied (e.g., attractive magnetic forces to collect the probe 100 in a portion of subsurface vasculature). The binding agents 120 each include one or more binding sites for the analyte such that the probe 100 is able to bind to multiple instances of the analyte.

The binding agents 120 may include a variety of substances configured to selectively interact with one or more analytes or other targets. For example, the binding agents 120 could include antibodies, aptamers (e.g., oligonucleotides, polypeptides), riboswitches, or some other elements configured to recognize and/or selectively bind to an analyte and/or an element of an analyte. The binding agents 120 could be configured to recognize and/or selectively bind to a membrane protein, a chemical moiety, an antigen, a surface feature, or some other element of an analyte. For example, the analyte could be an EV, and the binding agents 120 could include an antibody that is selective for a membrane protein that is characteristic of one or more types of EVs. The binding agents 120 could be covalently or otherwise chemically bound to the core 110 of the particle, could be adsorbed onto a surface of the core 110, or otherwise attached to the core 110 of the probe 100, to other binding agents 120 of the probe 100, or otherwise disposed on or within elements of the probe 100 such that the binding agents 120 can facilitate collection of instances of an analyte by binding such instances to the probe 100.

The binding agents 120 may selectively bind to a particular analyte or may bind to multiple different analytes. For example, the binding agents 120 may be configured or selected to bind to multiple different types of EVs (e.g., the binding agents 120 could include an anti-CD81 antibody, an anti-CD63 antibody, an anti-CD-9 antibody, or an anti-ALIX antibody). Alternatively, the binding agents 120 may include multiple different types of analyte-binding substances configured to bind to respective different analytes.

The core 110 includes one or more magnetic nanoparticles. Such magnetic nanoparticles could be composed of a variety of materials (e.g., superparamagnetic iron) disposed in a variety of geometries such that an attractive magnetic force can be exerted on the magnetic nanoparticles to collect the probe 100 (e.g., to collect the probe 100 in a portion of subsurface vasculature proximate a sensor or other elements of a body-mountable device). The magnetic nanoparticle(s) could be permanently magnetic, magnetizable, paramagnetic, superparamagnetic, or could have some other form of magnetism capable of facilitating the magnetic collection of the probe 100. The magnetic nanoparticle(s) could be magnetizable and could be further configured to be substantially nonmagnetic such that, in the absence of an applied external magnetic field, instances of the probe 100 substantially do not aggregate (e.g., such that instances of the probe do not aggregate in the vasculature unless an external magnetic field is applied to collect the probes). For example, the magnetic nanoparticle(s) could include superparamagnetic nanoparticles having a specified relaxation time or other magnetic property specified such that the magnetic nanoparticles become un-magnetized within a specified period of time after being magnetized by an external magnetic field.

The binding agents 120 could be bound directly to the surface of the one or more magnetic nanoparticles, e.g., by adsorption, covalent bonding, or some other method or mechanism of attaching the binding agents 120 to a surface of a magnetic nanoparticle. Additionally or alternatively, the magnetic nanoparticle(s) could have a coating and/or be disposed within a material (e.g., within a nanoparticle, a micelle, a lysosome, or some other structure) and the binding agents 120 could be adsorbed onto a surface of the material, could be covalently bound to the material, or could be otherwise attached to the material of the coating, nanoparticle, or other structure containing the magnetic nanoparticle(s).

The probe 100 and/or an aggregate of such probes could comprise one or more magnetic nanoparticles cores (e.g., 110) arranged in a configuration that maximizes the probability that the probe 100 and/or probe aggregate is captured in a portion of subsurface vasculature as a result of the application of a magnetic force by increasing the magnetic moment of the probe 100, and/or probe aggregate while minimizing fluid drag. In an example, a probe aggregate could be composed of an elongated train of probes 100 connected together by proteins, polysaccharides, or by some other means.

In some examples, the magnetic nanoparticle 110 could be encased within a polymer nanoparticle having a size, shape, elasticity, compliance, surface charge, deformability, and/or other properties specified such that the probe 100 can remain in circulation for a protracted period of time. Such nanoparticles could be formed to have a size that reduces excretion via the kidneys (e.g., a size larger than approximately 20 nanometer), the liver and/or spleen (e.g., a size smaller than approximately 200 nanometers), or via some other process. The probes 100 could have a size specified to increase the period of time over which the probe 100 remains in circulation while increasing the likelihood that the probe can be collected in a portion of subsurface vasculature by an applied magnetic force, e.g., the probe 100 could have a size between approximately 20 nanometers and approximately 10 microns. The probes 100 and/or probe aggregates could have a high elasticity and/or spheroidal, cuboidal, or rod-like aspect ratio to allow the probe 100 and/or probe aggregate to travel through small blood vessel by deforming or to provide some other functionality. For example, the probe 100 and/or probe aggregate could have a bulk elastic modulus between approximately 1 kilopascal and approximately 3000 kilopascals. In some examples, the probe 100 and/or probe aggregate could have a spheroidal or cuboidal shape (e.g., an aspect ratio approximately 1:1:1) or a rod-like shape (e.g., an aspect ratio approximately 1:1:1). The probe 100 could be coated with passivating agents (e.g. poly(ethylene glycol), various glycosaminoglycans) such that the probe 100 exhibits a net neutral charge or a nearly neutral charge.

The core 110 of the probe could be intrinsically detectable. For example, a magnetic field produced by one or more magnetic nanoparticles in the core 110 of the probe 100 could be detected by a sensor (e.g., by a magnetometer). This could include direct detection of the magnetic fields produced by the magnetic nanoparticle 110 of the probe 100 when magnetized by an external field, the detection of shifts or relaxation of the magnetic resonance of atomic spins of nuclei such as hydrogen that are located within the magnetic field produced by the magnetic nanoparticle 110, or by some other method. Additionally or alternatively, the probe 100 (e.g., the core 110) could include a fluorophore to enable the detection of the probe 100 in a portion of subsurface vasculature by a body-mounted device. This detection could provide for normalization of a detected signal related to an analyte (e.g., a fluorescence signal emitted from fluorescent reporters that are bound to instances of an analyte that are bound to the probe), increased specificity of detection of an analyte (e.g., by only counting detected instances of a fluorescent reporter that are co-located with a probe, as detected via fluorescence light emitted from the fluorophore of the probe), for distinguishing analyte-specific reporters that are bound to the analyte from residual unbound reporters, or could provide a signal for some other application.

Figure 1B:
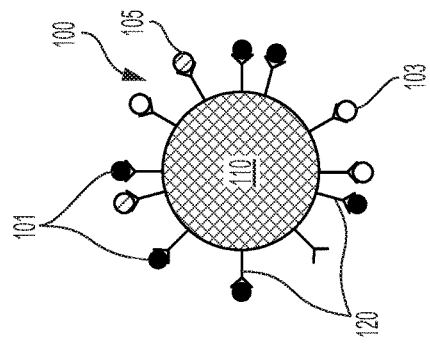
FIG. 1B is a schematic diagram of the probe of FIG. 1A, bound to multiple instances of multiple analytes, in accordance with an example embodiment.

The probe 100 could be introduced into the vasculature of a person and could then act, over a period of time, to collect instances of an analyte by binding the instances of the analyte to the probe 100 via the binding agents 120. This is illustrated by way of example in FIG. 1B. As shown in FIG. 1B, the binding agents 120 of the probe 100 have bound to multiple instances of a first analyte 101. The binding agents 120 have also bound to several instances of a second analyte 103 and a third analyte 105.

As noted above, the binding agents 120 could all be substantially the same and configured to bind to the multiple different types of analyte 101, 103, 105. For example, the different types of analyte 101, 103, 105 could be multiple types of EVs (e.g., different types of EVs produced by respective different types of tumors, cancer cells, or other tissues or cells). In such examples, the binding agents 120 could include a single type of antibody, aptamer, or other substance that is configured to bind the multiple different types of analytes. For instance, the different types of analyte 101, 103, 105 could be different types of EV and the binding agents could include anti-CD81 antibodies, anti-CD63 antibodies, anti-CD-9 antibodies, anti-ALIX antibodies, or some other substance(s) that are configured to bind to multiple different types of EVs or multiple different types of some other analytes of interest. Additionally or alternatively, the binding agents 120 could include multiple different types of binding agent (e.g., multiple different antibodies) configured to bind to respective different analytes and/or types of analytes.

To detect the analyte 101 (or one of the other analytes 103, 105 bound to the probe 100), the bound analyte could be detected directly, e.g., a color, an absorbance spectrum, an emission spectrum, a Raman spectrum, and excitation spectrum, or some other property of the analyte 101 could be detected. For example, the analyte 101 could be intrinsically fluorescent, and fluorescence light emitted from the analyte 101 could be detected and used to determine a presence, concentration, or other information about the analyte 101 in a body. Additionally or alternatively, a fluorescent reporter or other contrast agent that is configured to selectively bind to the analyte 101 could be introduced into the circulation and could bind to the analyte 101. The fluorescent reporter or other contrast agent could then be detected in order to detect the presence of the analyte. Such a fluorescent reporter or other contrast agent could be configured to selectively bind to a specific analyte (e.g., to a particular type of EV) or to multiple types of analyte.

Figure 1C:
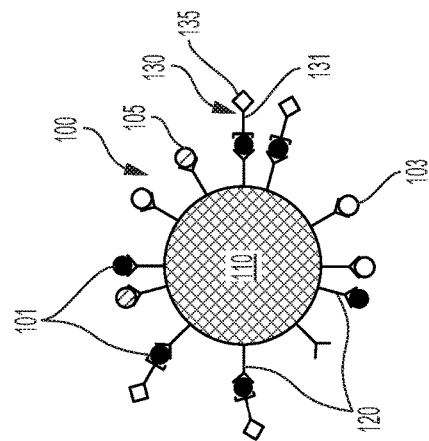
FIG. 1C is a schematic diagram of the probe and analytes of FIG. 1B, wherein multiple instances of a fluorescent reporter are bound to respective instances of an analyte that is bound to the probe, in accordance with an example embodiment.

As an illustrative example, FIG. 1C shows the probe 100 and instances of three analytes 101, 103, 105 bound thereto. Additionally, a fluorescent reporter 130 is present that is configured to selectively bind to the first analyte 101. The fluorescent reporter 130 includes a selective binding agent 131 configured to selectively bind to the first analyte 101 and a fluorophore 135 configured to emit fluorescence light in response to receiving illumination, e.g., to facilitate detection of the fluorescent reporter and/or detection of an instance of the analyte 101 to which the fluorescent reporter 130 is bound.

The selective binding agent 131 could include an antibody, an aptamer (e.g., an oligonucleotide, a polypeptide), a riboswitch, or some other element(s) configured to recognize and/or selectively bind to the analyte 101 and/or an element of the analyte 101. The binding agent 131 could be configured to recognize and/or selectively bind to a membrane protein, a chemical moiety, an antigen, a surface feature, or some other element of the analyte 101. For example, the analyte could be an EV, and the binding agent 131 could include an antibody that is selective for a membrane protein that is characteristic of a particular type of EV. For instance, the analyte 101 could be a HER2-overexpressing EV emitted from a breast carcinoma cell and the binding agent 131 could include an anti-HER2 antibody.

The fluorophore 135 could include a variety of substances that can be optically interrogated (e.g., illuminated with light having a specified wavelength or other specified property such that an intensity, wavelength, or other properties of light responsively emitted from the fluorophore can be detected and used to detect the fluorophore). For example, the fluorophore 135 could include a fluorescent protein, a dye, a Raman dye, a fluorescent small molecule, a fluorescent nanodiamond (e.g., a nanodiamond that includes one or more fluorescent defects or dopants), a fluorescent quantum dot, or some other substance that can be from outside of a portion of subsurface vasculature containing the fluorophore 135. In some examples, a fluorescence intensity, fluorescence wavelength, or other properties of the fluorophore 135 could be related to binding of the fluorescence reporter 130 to the analyte 101. Such a relationship could be related to a change in conformation of the fluorescence reporter 130 due to binding to the analyte 101 (e.g., a fluorescence intensity of the fluorophore 135 could be increased due to a change in distance between the fluorophore 135 and a quencher of the fluorescent reporter 130), due to proximity to magnetic nanoparticles of the probe 100 (e.g., a splitting of energy levels of a fluorescent center of a nanodiamond due to a magnetic field produced by magnetic nanoparticles of the probe 100), or to some other process or mechanism related to the binding of the fluorescence reporter 130 to the analyte 101.

The binding agent 131 could be covalently or otherwise chemically bound to the fluorophore 135 or to a coating or other material surrounding the fluorophore 135 (e.g., a material or layer formed on the surface of a fluorescent nanodiamond or quantum dot), the binding agent 131 could be adsorbed onto a surface of the fluorophore 135, the fluorophore 135 and binding agent 131 could both be attached to some other structure (e.g., a linking protein or nanoparticle), or the binding agent 131 could be attached to the fluorophore 135 in some other way to form the fluorescent reporter 130 such that the fluorescent reporter 130 can be used to detect the analyte 101.

The binding agent 131 may selectively bind to a particular analyte (e.g., 101). An instance of such a bound analyte may additionally be bound to a probe (e.g., probe 100) as described herein. As noted elsewhere herein, detection of the analyte 101 by detecting the fluorescent reporter 130 bound to the analyte may be facilitated by using a probe 100 to collect and concentrate multiple instances of the analyte 101 on the probe 100 and/or to magnetically collect the probe 100 in a portion of subsurface vasculature proximate a sensor. In some examples, a specificity of the detection of the analyte 101 could be increased by the probe 100 being configured to selectively bind to the analyte 101 in addition to the fluorescent reporter 130 being configured to selectively bind to the analyte 101. This could include the probe 100 and fluorescent reporter 130 both having respective different binding agents that are configured to selectively bind to the analyte 101, e.g., having respective different antibodies or other elements configured to bind to respective different proteins, chemical moieties, binding sites, or other aspects of the analyte 101.

Figure 1D:
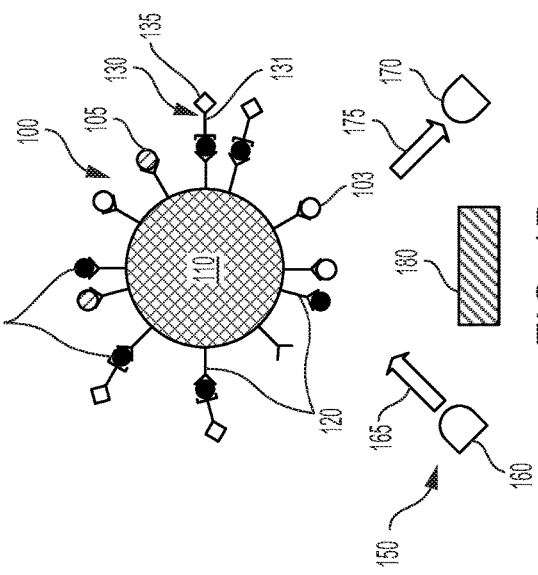
FIG. 1D is a schematic diagram of the probe, analytes, and fluorescent reporters of FIG. 1B as the fluorescent reporters are optically interrogated by a device, in accordance with an example embodiment.

As noted above, a property of the analyte 101 in a body (e.g., an amount of the analyte, a concentration of the analyte, a number of instances of the analyte, a rate of production/occurrence of the analyte) can be detected by detecting the fluorescent reporter 130 in a portion of subsurface vasculature. Such detection can include collecting the probe 100 (and any instances of the analyte 101 and/or fluorescent reporter 130 bound thereto) proximate to the sensor by exerting an attractive magnetic force on the probe 100. Such a sensor, and means for exerting such an attractive magnetic force, could be included in a body-mountable device that is configured to be mounted to an external body surface or otherwise maintained in proximity to the portion of subsurface vasculature. This is illustrated in FIG. 1D, which illustrates elements of a body-mountable device 150 disposed proximate to an environment (e.g., a portion of subsurface vasculature) containing the probe 100, the instances of the multiple analytes 101, 103, 105 bound to the probe 100, and the fluorescent reporter 130 bound to the analyte 101.

The body-mountable device 150 includes a magnetic flux source 180. The magnetic flux source 180 is configured to generate an attractive magnetic force on magnetic nanoparticle(s) of the probe 100. The generated magnetic force could be sufficient to collect the probe 100 in a portion of subsurface vasculature (or other environment of interest) proximate to the body-mountable device 150. The magnetic flux source 180 could include one or more electromagnets, permanent magnets, magnetic shims or poles, or other elements configured to generate, control, or focus a magnetic flux and/or a magnetic field. Further, the magnetic flux source 180 could be configured to change an amount of exerted magnetic force over time, e.g., to allow the probe 100 to circulate past the magnetic flux source 180 during a first period of time such that the probe 100 can travel throughout the circulatory system of a body, collecting instances of the analyte, and to collect the probe 100 during a second period of time, after the probe 100 has collected the analyte. This could include exerting a first magnetic force during a first period of time that is insufficient to collect the probe 100 (e.g., to exert substantially no magnetic force, e.g., by providing substantially no current to an electromagnetic of the magnetic flux source 180) and exerting a greater magnetic force (e.g., by generating a magnetic field having a strength of a few hundred Gauss) during a second period of time that is sufficient to collect the probe 100 (e.g., by generating a magnetic field having a strength of a few hundred Gauss).

The body-mountable device 150 includes a light emitter 160 and a light detector 170. Optical detection of the fluorescent reporters 130 (and/or of a fluorophore or other element of the probe 100) could include operating the light emitter 160 to emit illumination 165 to illuminate a portion of subsurface vasculature containing the probe 100 and operating the light detector 170 to detect light 175 emitted from the portion of subsurface vasculature. Such operation could allow for detection of an amount, concentration, number, or other properties of the analyte 101. Emitting illumination 165 could include emitting light having a specified wavelength or spectral content, e.g., to emit illumination at an excitation wavelength of a fluorophore 135 of the fluorescent reporter 130. Detecting light 175 emitted from the portion of subsurface vasculature could include detecting light at an emission wavelength of the fluorophore 135 of the fluorescent reporter 130.

Note that a relative timing of the introduction of the probe 100 into a body, the introduction of the fluorescent reporter 130 into the body, the collection of the probe 100 by the body-mountable device 150, the detection of the fluorescent reporter 130 and/or the analyte 101 bound thereto, or other operations as described herein could be specified according to an application. As described above, the probe 100 could be introduced before introduction of the fluorescent reporter 130. A difference in time between the introduction of the probe 100 and the introduction of the fluorescent reporter 130 could be specified to allow the probe 100 to travel throughout the vasculature of a body to collect multiple instances of the analyte 101 from a variety of tissues of the body. Further, the operation of the body-mountable device 150 to detect the fluorescent reporter 130 in a portion of subsurface vasculature and/or the mounting of the body-mountable device 150 to an external body surface proximate a portion of subsurface vasculature could occur before, during, and/or after introduction of the fluorescent reporter 130 into a body. For example, the body-mountable device 150 could operate to detect an amount of the fluorescent reporter 130 in a portion of subsurface vasculature immediately after introduction of the fluorescent reporter 130 into the body in order to determine a baseline amount or concentration of the fluorescent reporter 130 in the body and/or a time constant of the inactivation or removal of the fluorescent reporter 130 from the body. Such a determined baseline could be used to normalize an amount of the fluorescent reporter 130 that is detected at a later point in time in order to determine an amount of the analyte 101 that is present in the body and/or in the portion of subsurface vasculature.

As shown, a single type of fluorescent reporter 130 is present and is configured to selectively bind to the first analyte 101. Additional fluorescent reporters could be introduced to facilitate the detection of other analytes (e.g., 103, 105). Such additional fluorescent reporters could have respective different binding agents (configured to bind to respective different analytes) and could differ with respect to an excitation spectrum, an excitation wavelength, an emission spectrum, an emission wavelength, a fluorescence lifetime, or some other property such that the body-mountable device 150 could detect the different fluorescent reporters in a portion of subsurface vasculature. This could include the light emitter 160 emitting illumination 165 at a number of different wavelengths, e.g., wavelengths that correspond to excitation wavelengths of the different fluorophores of the different fluorescent reporters. Additionally or alternatively, detecting the different fluorescent reporters could include using the light detector 170 to detect light at a variety of different wavelengths, e.g., wavelengths that correspond to emission wavelengths of the different fluorophores of the different fluorescent reporters.

Alternatively, a number of different analytes (e.g., 101, 103, 105) could be detected by introducing respective different fluorescent reporters at respective different points in time. Each of the fluorescent reporters could be present and/or detectable in a body for a specified period of time related, e.g., to a rate of removal of the reporters from the vasculature of the body (e.g., by the kidneys, by deposition into tissues from the vasculature), to a rate of decomposition or otherwise reduction in fluorescence intensity of the fluorophores (e.g., by the activity of the immune system of the body), or by some other mechanism. The body-mountable device 150 could be used, during respective different periods of time, to detect the different fluorescent reporters in a portion of subsurface vasculature. As the presence of such different fluorescent reporters in the vasculature is separated into different time periods, the different fluorescent reporters could include fluorophores that have similar excitation wavelengths, similar emission wavelengths, or that are similar in some other way with respect to detection. For example, the different fluorescent reporters could each include the same fluorophore attached to respective different binding agents (e.g., antibodies) that are configured to bind with respective different analytes.

A detected amount, presence, concentration, number, rate of emission/occurrence, or some other information about an analyte (e.g., 101, 103, 105) could be used to determine information about a body, e.g., to determine a health state of the body. In some examples, the analyte could be related to cancer cells in the body (e.g., the analyte could be an EV that is characteristically produced by a particular type of cancer cell and/or that includes surface markers or has some other property indicative of a particular type of cancer) and detected information about the analyte could be used to determine information about the cancer cells. For example, the information about the analyte could be used to determine that a tumor is present, a size of a tumor, a degree or rate of metastasis of a tumor, a stage of a tumor, or some other information about the presence or status of a tumor.

A body-mountable device (e.g., 150) that is configured to magnetically collect a probe and/or to detect a fluorescent reporter, as described herein, could be configured in a variety of ways. The body-mountable device could include a mounting surface or be otherwise configured to mount to an external body surface proximate to a portion of subsurface vasculature such that a sensor and/or a magnetic flux source of the body-mountable device are located proximate the portion of subsurface vasculature (e.g., to facilitate exertion of magnetic forces on probes in the portion of subsurface vasculature and/or to facilitate detection of fluorescent reporters in the portion of subsurface vasculature). The body-mountable device could be handheld, and could be maintained in contact with an external body surface manually. In another example, the body-mountable device could be a desktop device, a wall-mounted device, or some other device that an external body surface of a person could be brought into contact with, e.g., an arm of a person could be placed into contact with such a body-mountable device such that a sensor and/or magnetic flux source are proximate a portion of subsurface vasculature within the arm (e.g., to facilitate detection of fluorescent reporters in the portion of subsurface vasculature by the sensor and/or to facilitate collection of probes in the portion of subsurface vasculature proximate the sensor by the magnetic flux source).

In some examples, the body-mountable device could be a wearable device (e.g., a wrist-mounted device) that includes a strap, an adhesive, or some other mounting means configured to allow the device to be worn on an external surface of a body. Such a wearable body-mountable device could be worn over a protracted period of time, e.g., to allow for detection of fluorescent reporters, collection of probes, or some other functions over the protracted period of time. Such protracted operation to detect, collect, or otherwise interact with probes, fluorescent reporters, analytes, or other contents of a portion of subsurface vasculature or other body tissue(s) could allow for the detection of rare and/or low-concentration analytes, the collection of a plurality of probes (and any instances of an analyte and/or fluorescent reporter bound thereto), or allow for some other operations.

Figure 2:
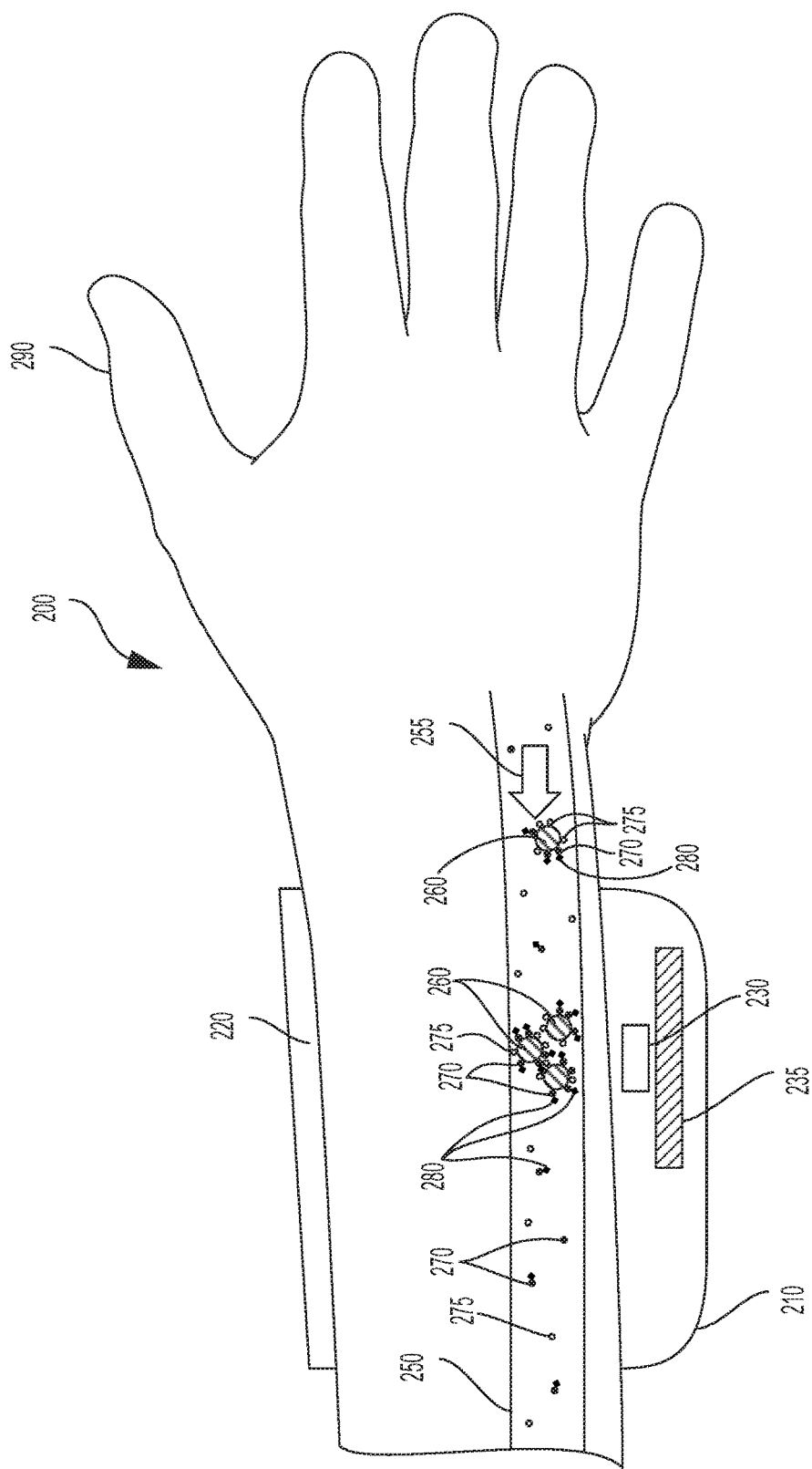
FIG. 2 is a side cross-sectional view of probes and fluorescent reporters in a portion of subsurface vasculature and a device positioned proximate to the portion of subsurface vasculature, in accordance with an example embodiment.

An example wearable body-mountable device is illustrated in FIG. 2. FIG. 2 illustrates example probes 260, fluorescent reporters 280, a first analyte 270, and a second analyte 275 disposed in a blood vessel 250 (i.e., a portion of subsurface vasculature). The probes 260 are each configured to bind to multiple instances of the first 270 and second 275 analytes and each include one or more magnetic nanoparticles to facilitate the exertion of magnetic forces (e.g., attractive magnetic forces) on the probes 260. The fluorescent reporters 280 are configured to selectively bind to the first analyte 270 and include a fluorophore, a dye, a Raman dye, a quantum dot, a fluorescent nanodiamond, or some other element or substance that can be used to detect the fluorescent reporters 280 by illuminating the portion of subsurface vasculature 250 (e.g., with light of an excitation wavelength of the fluorescent reporters 280) and detecting light responsively emitted from the portion of subsurface vasculature 250 (e.g., light emitted from the fluorescent reporters 280 at an emission wavelength of the fluorescent reporters 280).

In this example, disposed in blood vessel 250 are instances of a first analyte 270 (e.g., a first type of EV) and a second analyte 275 (e.g., a second type of EV) of which some instances of each of the first 270 and second 275 analyte are bound to several probes 260. As illustrated, each of the probes 260 may be bound to one or more of each of the analytes 270, 275. Also disposed in blood vessel 250 are unbound instances of the first 270 and second 275 analytes. The fluorescent reporter 280 is also present in the blood vessel 250 and may be bound to instances of the first analyte 270 that are bound to a probe 260 or that are unbound. The blood vessel 250 is located in an arm 290 and contains blood that is flowing (direction of flow indicated by the arrow 255).

The wearable body-mountable device 200 includes a housing 210 mounted outside of or otherwise proximate to the blood vessel 250 by a mount 220 configured to encircle the arm 290. The body-mountable device 200 includes a magnetic flux source 235 (e.g., a permanent magnet, an electromagnet) configured to exert an attractive magnetic force on the probes 260 (e.g., on magnetic nanoparticles of the probes 260) in the blood vessel 250 that are proximate the magnetic flux source 235 (e.g., that are within a first location of subsurface vasculature that is proximate the magnetic flux source 235). The body-mountable device 200 also includes a sensor 230 that is configured to detect the fluorescent reporters 280 in the blood vessel 250 that are proximate the sensor 250.

The sensor 230 could include a light emitter and/or a light detector configured to detect a presence, an amount, a location, a concentration, or some other property of the fluorescent reporter 280 proximate the sensor 230. The binding of the fluorescent reporter 280 to instances of the first analyte 270, the binding of such instances of the first analyte 270 to probes 260, and the collection of such probes 260, by exertion of an attractive magnetic force by the magnetic flux source 235, proximate the sensor 230 can increase an intensity of a light emitted from the fluorescent reporters 280 that is detected by the sensor 230. A detected amount of the fluorescent reporter 280 could be used to determine an amount of the first analyte 270 that is present in the blood vessel 250. Thus, a detected amount of the fluorescent reporter 280 could be used to determine a health state related to the first analyte 270, e.g., to determine a presence or status of a tumor that characteristically produces the first analyte 270 (e.g., a tumor that characteristically produces a particular type of EV).

As shown in FIG. 2, the magnetic flux source 235 is producing an attractive magnetic force sufficient to collect the probes 260 in the blood vessel 250 proximate the magnetic flux source 235 and sensor 230. However, the magnetic flux source 235 could be operated to produce different amounts of magnetic force at different points in time. Such operation could include controlling a current applied to an electromagnet and/or rotating or otherwise mechanically actuating a permanent magnet, a magnetic pole, a magnetic shim, or some other magnetic element(s) of the magnetic flux source 235. Such operation to change the magnetic force exerted by the magnetic flux source 235 could be performed to facilitate a variety of functions, e.g., to allow the probes 260 to pass through the blood vessel 250 during a first period of time such that the probes 260 can travel throughout the vasculature of a person to collect instances of one or more analytes (e.g., 270, 275) and to collect the probes 260 during a subsequent period of time.

Note that the configuration of the elements of the body-mountable device 200 is intended as a non-limiting example embodiment. As shown, the magnetic flux source 235 is disposed to exert an attractive magnetic force to collect the probes 260 proximate the sensor 230, which is located between the magnetic flux source 235 and the skin of the arm 920. However, the sensor 230 could be located at other locations relative to the magnetic flux source 235, e.g., to the side of the magnetic flux source 235. Further, the magnetic flux source 235 could include a window or hole, and the sensor 230 could be located within such a window or hole. In some examples, the sensor 230 could be located downstream from the magnetic flux source 235. In such examples, the magnetic flux source 235 could be operated, during a first period of time, to collect the probes 260 (e.g., forming a cluster of collected probes 260 in the blood vessel 250 proximate to the magnetic flux source 235). Subsequently, the magnetic flux source 235 could release the collected probes (e.g., by reducing a current applied to an electromagnet, by rotating or otherwise mechanically actuating one or more magnetic components of the magnetic flux source 235) and the released probes could flow downstream, past the sensor 230. The sensor could then operate to detect the fluorescent reporters 280 that are bound (via binding to instance of the analyte 270) to the released probes 260 as the released probes 260 flow (with the flow of the blood 255) past the sensor 230. Other configurations and operations of a body-mountable device are anticipated.

III. Example Body-Mountable Devices

Body-mountable devices as described herein can be configured to be mounted to an external body surface of a person and to enable a variety of applications and functions including the detection and/or collection of analytes as described elsewhere herein that are disposed in the body of the person (e.g., disposed in a portion of subsurface vasculature of the person) and that have a property (e.g., an amount or number of the probe that is present in a portion of vasculature, a rate, frequency, or timing of the probe being present in a portion of vasculature) that is related to a health state of the person (e.g., to the presence or status of a tumor in the body of the person). Such devices could include one or more sensors configured to detect a fluorescent reporter that is configured to selectively bind to the analyte in the portion of subsurface vasculature and/or to exert an attractive magnetic force to collect a probe in the portion of subsurface vasculature that is bound to multiple instances of the analyte.

A wearable body-mountable device 300 (illustrated in FIG. 3) can be provided to detect fluorescent reporters that are configured to selectively bind to an analyte of interest that are disposed in a wearer's body (e.g., disposed in portions of subsurface vasculature proximate the device 300) and to exert a magnetic force to collect probes that include magnetic nanoparticles and that are configured to bind to multiple instances of such an analyte of interest. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature or other targets or elements of the body of the wearer are easily observable, the qualification of which will depend on the type of detection system used. The device may be placed in close proximity to the skin or tissue. A mount 310, such as a belt, wristband, ankle band, etc. can be provided to mount the device at, on or in proximity to the body surface. The mount 310 may prevent the wearable device from moving relative to the body to reduce measurement error and noise. In one example, shown in FIG. 3, the mount 310, may take the form of a strap or band 320 that can be worn around a part of the body. Further, the mount 310 may be an adhesive substrate for adhering the wearable device 300 to the body of a wearer.

A housing 330 is disposed on the mount 310 such that it can be positioned on the body. A contact surface 340 of the housing 330 is intended to be mounted facing to the external body surface. The housing 330 may include a magnetic flux source 355 for producing a magnetic field sufficient to collect probes that are disposed in the body of the wearer and that include magnetic nanoparticles. The housing 330 may additionally include a sensor 350 for illuminating and/or detecting light produced by fluorescent reporters disposed in the body of the wearer. The housing 330 could be configured to be water-resistant and/or water-proof.

The magnetic flux source 355 is configured to produce a magnetic field sufficient to collect magnetic nanoparticle-containing probes disposed proximate to the magnetic flux source 355 in an environment of interest, e.g., a portion of subsurface vasculature of a wearer. For example, the magnetic flux source 355 could be configured to produce a magnetic field having a magnitude of several hundred Gauss (e.g., greater than approximately 100 Gauss) at a distance of approximately 1 centimeter from the contact surface 340 (e.g., a distance within which a portion of subsurface vasculature containing the probes may be located when the device 300 is mounted to a body). The magnitude of the magnetic field produced by the magnetic flux source 355 and the dimensions of the magnetic flux source 355 (e.g., the length of the magnetic flux source 355 in a direction aligned with a direction of blood flow within the portion of subsurface vasculature) could be specified such that magnetic nanoparticle-containing probes flowing in the body proximate to the magnetic flux source 355 are collected proximate the magnetic flux source 355.

The magnetic flux source 355 could be configured to collect such probes and/or to release such collected probes, e.g., to facilitate extraction of the collected probes (and any instances of an analyte of interest that may be bound to such probes) from the body, to provide a higher-magnitude optical signal for the sensor 350 to detect, or according to some other application. The magnetic flux source 355 could include one or more electromagnets, permanent magnets, or other magnetic producing elements. Further, the magnetic flux source 355 could be configured and/or operated to change a magnetic field produced by the magnetic flux source 355, e.g., to release collected probes such that the collected probes can be transported, by a blood flow, past the sensor 330, or according to some other application. This could include changing a current applied to an electromagnet of the magnetic flux source 355, mechanically actuating an electromagnet, permanent magnet, or other flux producing element of the magnetic flux source 355, or performing some other operation(s). Note that the magnetic flux source 355 could be configured to provide some other functionality, e.g., to magnetize the magnetic nanoparticles of the probes.

The sensor 350 is configured to detect the presence, number, concentration, location, or other properties of fluorescent reporters as described elsewhere herein that are located in an environment of interest, e.g., a portion of subsurface vasculature of a wearer. The sensor 350 could include a light detector configured to detect an intensity, wavelength, spectral content, polarization, or other properties of light emitted from such fluorescent reporters, e.g., light reflected or scattered by a chromophore, dye, or Raman dye of a probe or light fluorescently emitted from a fluorescent organic compound, a fluorescent defect in a nanodiamond, or some other fluorescent element of a fluorescent reporter. Further, the sensor 350 could include one or more light emitters configured to emit light having a specified intensity, polarization, wavelength, spectral content, or some other specified property in order to optically interrogate the fluorescent reporters, e.g., to illuminate the fluorescent reporters or to excite a fluorophore of the fluorescent reporters.

The wearable device 300 may also include a user interface 390 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 390 may include a display 392 where a visual indication of the alert or recommendation may be displayed. The display 392 may further be configured to provide an indication of the presence or properties of one or more detected analytes and/or a presence or status of a tumor in the body of the wearer or some other determined health state of the body of the wearer.

Figure 3:
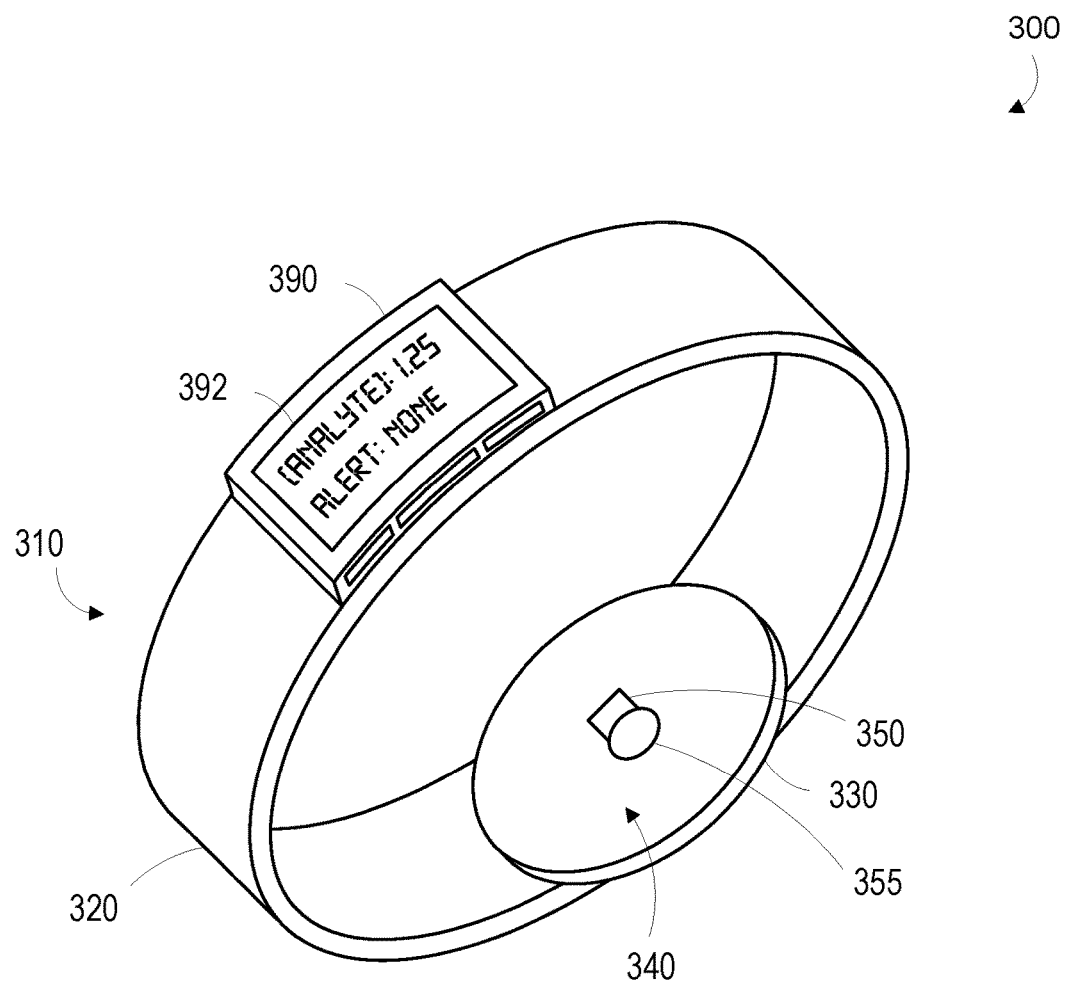
FIG. 3 is perspective view of an example device.

Note that example devices herein are configured to be mounted to a wrist of a wearer. However, the embodiments described herein could be applied to other body parts (e.g., an ankle, a thigh, a chest, a forehead, a thigh, a finger), or to detect an analyte, using probes and fluorescent reporters as described herein, in other environments. Further, while the body-mountable device 300 of FIG. 3 is illustrated as a wearable device that is configured to be mounted to an external body surface of a person and to be worn by a person, body-mountable devices as described herein could take other forms. For example, body-mountable devices could include hand-held devices configured to be manually mounted to an external body surface of a person (e.g., a wrist surface) such that a sensor of the body-mountable device is proximate to a portion of subsurface vasculature beneath the external body surface. Additionally or alternatively, a body-mountable device may be a desktop or otherwise configured device that a body part can be brought into contact with (e.g., against which an arm may be positioned) such that a sensor of the body-mountable device is proximate to a portion of subsurface vasculature beneath an external body surface of the body part.

The term "body-mountable device," as used in this disclosure, refers to any device that is capable of being mounted at, on or in proximity to a body surface and/or a device (e.g., a desktop device) that a body part (e.g., an arm) can be brought into contact with such that a surface of the body part is mounted at, or in proximity to, the device. In order to take in vivo measurements in a non-invasive manner from outside of the body, the body-mountable device may be positioned on a portion of the body where subsurface vasculature or other targets or elements of the body of the wearer are easily observable, the qualification of which will depend on the type of detection system used. Additionally or alternatively, a portion of the body may be positioned on or within the body-mountable device such that subsurface vasculature or other targets or elements of the body of the wearer are easily observable Body-mountable devices and other embodiments as described herein can include a variety of components configured in a variety of ways. Devices described herein could include electronics including a variety of different components configured in a variety of ways to enable applications of the body-mountable device. The electronics could include controllers, amplifiers, switches, display drivers, touch sensors, wireless communications chipsets (e.g., Bluetooth radios or other radio transceivers and associated baseband circuitry to enable wireless communications between the body-mountable device and some other system(s)), or other components. The electronics could include a controller configured to operate one or more magnetic flux sources and/or sensors to collect and/or release probe(s) in a portion of subsurface vasculature, to detect a light, a magnetic field, or some other physical variable relating to a fluorescent reporter and/or probe in a portion of subsurface vasculature, and/or to detect some other properties of a user or to perform some other functions. The controller could include a processor configured to execute computer-readable instructions (e.g., program instructions stored in data storage of the body-mountable device) to enable applications of the body-mountable device. The electronics can include additional or alternative components according to an application of the body-mountable device.

Body-mountable devices as described herein could include one or more user interfaces. A user interface could include a display configured to present an image to a user and to detect one or more finger presses of a user on the interface. The controller or some other component(s) of the electronics could operate the user interface to provide information to a user or other user of the device and to enable the user or other user to affect the operation of the body-mountable device, to determine some property of the body-mountable device and/or of the user of the body-mountable device (e.g., a presence or status of a tumor in the body of a user of the body-mountable device and/or some other health state of the user), or to provide some other functionality or application to the user. As one example, the user could press an indicated region of the user interface to indicate that an amount of probes and/or fluorescent reporters have been introduced into the body of the user. Other indicated information, changes in operation of the body-mountable device, or other functions and applications of the user interface are anticipated.

Note that the embodiments illustrated in the Figures are illustrative examples and not meant to be limiting. Alternative embodiments, including more or fewer components in alternative configurations are anticipated. A body-mountable device could include multiple housings or other such assemblies each containing some set of components to enable applications of such a body-mountable device. For example, a body-mountable device could include a first housing within which are disposed one or more magnetic flux sources configured to collect magnetic nanoparticle-containing probes that are disposed in the user's body (e.g., within portions of subsurface vasculature of the user) and one or more sensors configured to detect fluorescent reporters that are disposed in the user's body (e.g., to detect such reporters that are bound to instances of an analyte that are bound to probes that have been collected proximate the sensor by the magnetic flux source). The body-mountable device could additionally include a second housing containing a user interface and electronics configured to operate the magnetic flux source(s) and sensor(s) and to present information to and receive commands from a user of the body-mountable device. A body-mountable device could be configured to perform a variety of functions and to enable a variety of applications. Body-mountable devices could be configured to operate in concert with other devices or systems; for example, body-mountable devices could include a wireless communication interface configured to transmit data indicative of one or more properties of the body of a user of the body-mountable device. Other embodiments, operations, configurations, and applications of a body-mountable device as described herein are anticipated.

Figure 4:
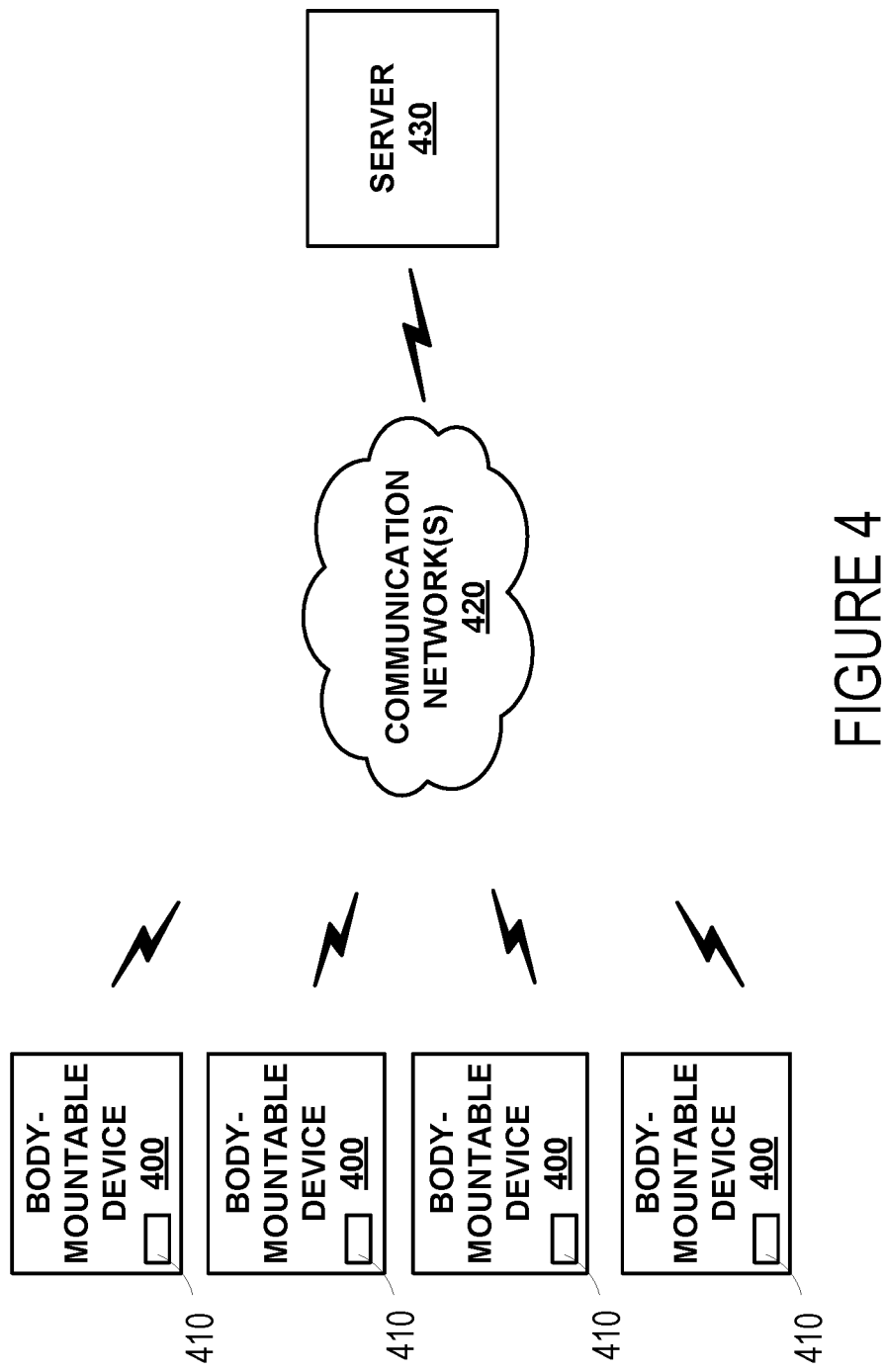
FIG. 4 is an illustration of a number of body-mountable devices in communication with a server, in accordance with an example embodiment.

FIG. 4 is a simplified schematic of a system including one or more body-mountable devices 400. The one or more body-mountable devices 400 may be configured to transmit data via a communication interface 410 over one or more communication networks 420 to a remote server 430. In one embodiment, the communication interface 410 includes a wireless transceiver for sending and receiving communications to and from the server 430. In further embodiments, the communication interface 410 may include any means for the transfer of data, including both wired and wireless communications. For example, the communication interface may include a universal serial bus (USB) interface or a secure digital (SD) card interface. Communication networks 420 may be any one of may be one of: a plain old telephone service (POTS) network, a cellular network, a fiber network and a data network. The server 430 may include any type of remote computing device or remote cloud computing network. Further, communication network 420 may include one or more intermediaries, including, for example wherein the body-mountable device 400 transmits data to a mobile phone or other personal computing device, which in turn transmits the data to the server 430.

In addition to receiving communications from the body-mountable device 400, such as a detected presence, concentration, or amount of a fluorescent reporter and/or analyte in a portion of subsurface vasculature, a rate, frequency, or timing of the presence of such reporters and/or analytes in a portion of subsurface vasculature and/or information determined therefrom (e.g., information about the presence or status of a tumor in the body of a user) or other collected physiological properties and data, the server may also be configured to gather and/or receive either from the body-mountable device 400 or from some other source, information regarding a user's overall medical history, environmental factors and geographical data. For example, a user account may be established on the server for every user that contains the user's medical history. Moreover, in some examples, the server 430 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a user's health state from a hospital or physician. Such information may be used in the server's decision-making process, such as recognizing correlations and in generating clinical protocols.

Additionally, the server may be configured to gather and/or receive the date, time of day and geographical location of each user of the device during each measurement period. Such information may be used to detect and monitor spatial and temporal spreading of diseases. As such, the body-mountable device may be configured to determine and/or provide an indication of its own location. For example, a body-mountable device may include a GPS system so that it can include GPS location information (e.g., GPS coordinates) in a communication to the server. As another example, a body-mountable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a user of the device and, at least in part, the detection of the presence or other properties of probes in the vasculature of a user and the indicated health state of the user. From this information, the server may be configured to derive an indication of the effectiveness of the drug or treatment. For example, a body-mountable device may be configured to detect the presence or status of a tumor by detecting properties of fluorescent reporters that are configured to selectively bind to EVs or to some other analyte related to the tumor and/or cells of the tumor. If a user is prescribed a drug intended to destroy tumor cells, but the server receives data from the body-mountable device indicating that, e.g., the amount of the analyte in the user's blood has been increasing over a certain number of measurement periods, the server may be configured to derive an indication that the drug is not effective for its intended purpose for this user.

Further, some embodiments of the system may include privacy controls which may be automatically implemented or controlled by the user of the device. For example, where a user's collected analyte and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, users of a device may be provided with an opportunity to control whether or how the device collects information about the user (e.g., information about a user's medical history, social actions or activities, profession, a user's preferences, or a user's current location), or to control how such information may be used. Thus, the user may have control over how information is collected about him or her and used by a clinician or physician or other user of the data. For example, a user may elect that data, such as health state and detected probe data, collected from his or her device may only be used for generating an individual baseline and recommendations in response to collection and comparison of his or her own data and may not be used in generating a population baseline or for use in population correlation studies.

IV. Example Electronics Platform for a Device

Figure 5:
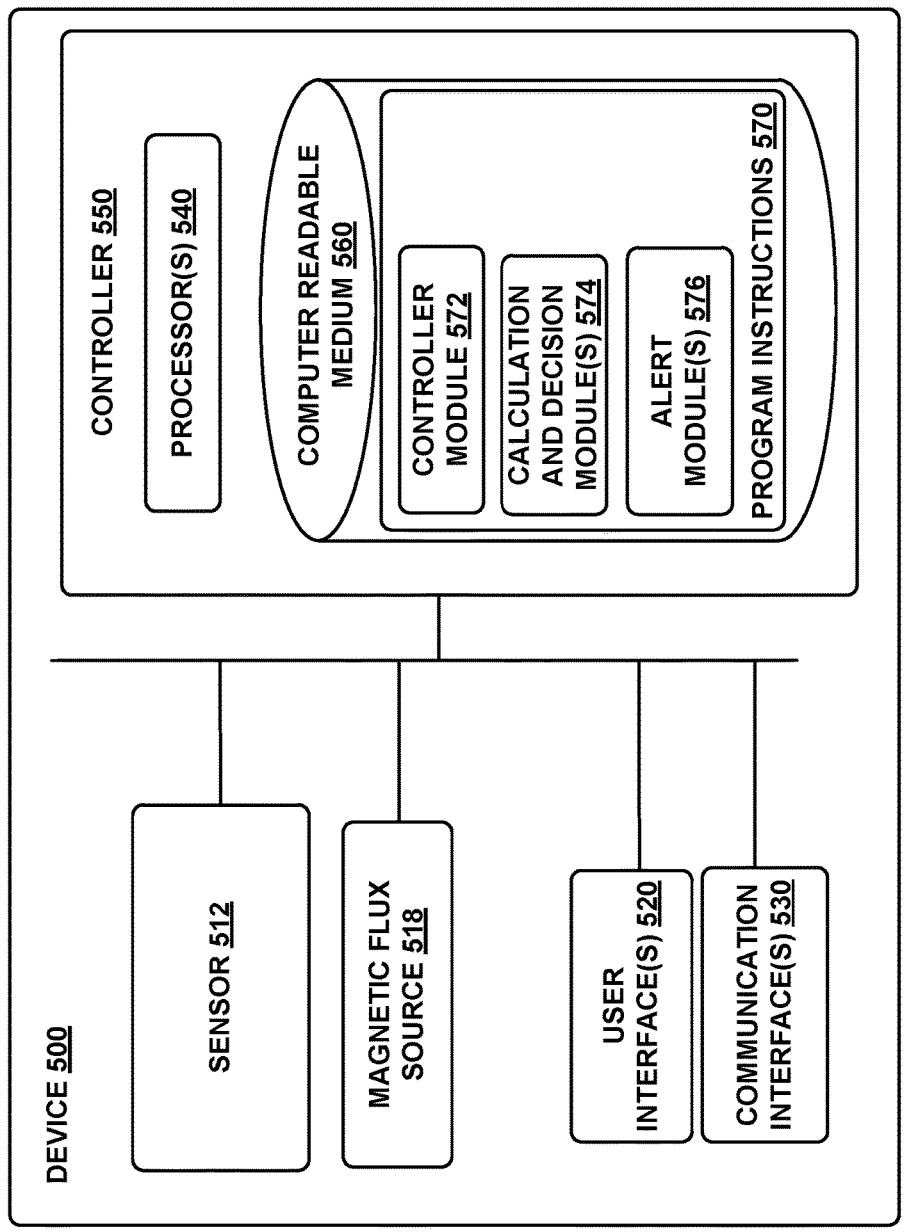
FIG. 5 is a block diagram of an example device.

FIG. 5 is a simplified block diagram illustrating the components of a device 500, according to an example embodiment. Device 500 may take the form of or be similar to one of the wearable and/or body-mountable devices 150, 200, or 300 shown in FIGS. 1D, 2, and 3. However, device 500 may also take other forms, such as an ankle, waist, or chest-mounted device. Device 500 also could take other forms. For purposes of illustration, device 500 is described with reference to probes 260, analytes 270, 275, and fluorescent reporters 280 in a blood vessel 250, as shown in FIG. 2.

In particular, FIG. 5 shows an example of a device 500 having a sensor 512, a magnetic flux source 518, a user interface 520, communication interface 530 for transmitting data to a remote system, and a controller 550. The components of the device 500 may be disposed on a mount or on some other structure for mounting the device to enable stable detection of one or more properties (e.g., a light or some other physical variable) related to the presence or other properties of an analyte and/or a fluorescent reporter as described elsewhere herein that is present in a body of a user of the device 500). For example, the device 500 could include a structure configured for mounting the device 500 to an external body surface where one or more portions of subsurface vasculature or other anatomical elements are readily observable.

Controller 550 may be provided as a computing device that includes one or more processors 540. The one or more processors 540 can be configured to execute computer-readable program instructions 570 that are stored in the computer readable data storage 560 and that are executable to provide the functionality of a device 500 described herein.

The computer readable medium 560 may include or take the form of one or more non-transitory, computer-readable storage media that can be read or accessed by at least one processor 540. The one or more computer-readable storage media can include volatile and/or non-volatile storage components, such as optical, magnetic, organic or other memory or disc storage, which can be integrated in whole or in part with at least one of the one or more processors 540. In some embodiments, the computer readable medium 560 can be implemented using a single physical device (e.g., one optical, magnetic, organic or other memory or disc storage unit), while in other embodiments, the computer readable medium 560 can be implemented using two or more physical devices.

The sensor 512 (e.g., a light sensor, a light emitter, and/or some other elements) that is configured to detect the fluorescent reporters 280 in the blood vessel 250 that are proximate the sensor 512. Such detection can include detecting that the fluorescent reporter(s) 280 are present in the blood vessel 250, determining a number, concentration, or amount of the fluorescent reporter 280 in the blood vessel 250 and/or determining properties of the fluorescent reporter 280 in the blood vessel 250.

The sensor 512 could be configured to detect a variety of physical properties in order to detect the presence of the fluorescent reporters 280 that are located proximate the sensor 512 in a body of a user of the device 500 and/or to detect one or more properties of the analyte 270 to which the fluorescent reporters 280 are configured to selectively bind. This could include detecting properties of light that is emitted from fluorophores, chromophores, dyes, Raman dyes, fluorescent nanodiamonds, fluorescent quantum dots, magnetic nanoparticles, or other detectable elements of the fluorescent reporters 280. The sensor 512 could include a light detector (e.g., a photodiode, a phototransistor, an avalanche photodiode, a CCD sensor, a camera, a spectrometer) that is configured to detect the intensity, polarization, wavelength, spectral content, degree of coherence, or other properties of light received from the fluorescent reporters 280. Further, the sensor 512 could include one or more light emitters configured to illuminate the fluorescent reporters 280 and/or an environment that could contain the fluorescent reporters 280, e.g., to excite a fluorophore of the fluorescent reporters 280, to interrogate a color or absorbance spectrum of the fluorescent reporters 280, or to interrogate some other optical property of the fluorescent reporters 280.

The magnetic flux source 518 is configured to produce a magnetic field sufficient to collect magnetic nanoparticle-containing probes 260 (e.g., by exerting an attractive magnetic force). The collected probes 260 could be collected in a body (e.g., in a portion of subsurface vasculature) such that the presence or some other property of an analyte bound to the probes 260 could be detected by the sensor 512 (e.g., by detecting fluorescent reporters bound to instances of the analyte that are bound to the probes). In some examples, the magnetic flux source 518 could be configured to control a magnitude of the produced attractive magnetic force, e.g., to subsequently release such collected probes 260 such that any fluorescent reporters 280 bound to the probes 260 (e.g., via binding to instances of the analyte 270 that are in turn bound to the probes 260) can be detected by the sensor 512 (e.g., by being transported by a flow of blood within a portion of subsurface vasculature from the proximity of the magnetic flux source 518 to the sensor 512). Additionally or alternatively, the sensor 512 could be configured to detect fluorescent reporters 280 that are bound to the probes 260 when the magnetic flux source 518 is exerting a magnetic force to collect the probes 260 (e.g., by emitting illumination and receiving responsively emitted light through the magnetic flux source 518, from beneath the magnetic flux source 518, and/or from beside the magnetic flux source 518). The magnetic flux source 518 could also be configured to magnetize magnetic nanoparticles of the probes 260. The magnetic flux source 518 could include one or more permanent magnets and/or electromagnets.

Note that a device could include a subset of the elements described here, e.g., a device could lack a magnetic flux source and/or some other combination of elements. Further, a device could include multiple of one or more illustrated elements. For example, a device could include multiple sensors 512 configured to detect a light or some other physical variables at respective multiple different locations and/or in multiple different directions. In some examples, multiple illustrated elements of the device 500 could be implemented as the same component and/or share some component(s) in common.

The program instructions 570 stored on the computer readable medium 560 may include instructions to perform any of the methods described herein. For instance, in the illustrated embodiment, program instructions 570 include a controller module 572, calculation and decision module 574 and an alert module 576.

The controller module 572 may include instructions for operating the sensor 512, magnetic flux source 518, and/or some other components to detect fluorescent reporters (e.g., to detect the presence, location, amount, or other properties) and/or analytes bound thereto in a portion of subsurface vasculature proximate the sensor 512 and/or to magnetically collect such analytes that are bound to magnetic probes in the portion of subsurface vasculature (e.g., by exerting an attractive magnetic force on such probes).

The calculation and decision module(s) 574 may include instructions for analyzing data generated by the sensor 512 to determine information about an analyte in a body (e.g., by detecting the presence, in a portion of subsurface vasculature, of fluorescent reporters that are configured to selectively bind to the analyte) or other information (e.g., health states) of a body of a user of the device 500, such as a presence or status of a tumor in the body of the user. Calculation and decision module 574 can additionally include instructions for analyzing the data to determine if a medical condition or other specified condition is indicated, or other analytical processes relating to the environment proximate to the device 500.

In particular, if the fluorescent reporters are configured to selectively bind to an analyte that is related to a tumor (e.g., a particular type of EV or other analyte that is produced by cells of a tumor or whose presence is otherwise indicative to the presence or status of a tumor), the calculation and decision module(s) 574 may include instructions for determining the presence of a tumor, a size of a tumor, a type of a tumor (e.g., if the fluorescent reporters are configured to selectively bind to an analyte that is produced by or otherwise indicative of a particular tumor type), a rate or degree of metastasis of a tumor, or some other information about the presence or status of a tumor. Such determinations could be made based on an amount of the detected fluorescent reporters and/or the analyte bound thereto, a rate or frequency at which the analyte is detected, and/or a timing of detection of the analyte and/or fluorescent reporters relative to, e.g., introduction of the fluorescent reporters and/or magnetic nanoparticle-containing probes into the body.

The controller module 572 can also include instructions for operating a user interface 520. For example, controller module 572 may include instructions for displaying data collected by the sensor 512 and analyzed by the calculation and decision module 574, or for displaying one or more alerts generated by the alert module 576. Controller module 572 may include instructions for displaying data related to an analyte in one or more portions of subsurface vasculature that have been detected using the sensor 512 or some other detected and/or determined health state of a user. Further, controller module 572 may include instructions to execute certain functions based on inputs accepted by the user interface 520, such as inputs accepted by one or more buttons disposed on the user interface.

Communication interface 530 may also be operated by instructions within the controller module 572, such as instructions for sending and/or receiving information via a wireless antenna, which may be disposed on or in the device 500. The communication interface 530 can optionally include one or more oscillators, mixers, frequency injectors, etc. to modulate and/or demodulate information on a carrier frequency to be transmitted and/or received by the antenna. In some examples, the device 500 is configured to indicate an output from the processor by modulating an impedance of the antenna in a manner that is perceivable by a remote server or other remote computing device.

The program instructions of the calculation and decision module 574 may, in some examples, be stored in a computer-readable medium and executed by a processor located external to the device 500. For example, the device 500 could be configured to collect certain data, generated by the sensor 512, regarding fluorescent reporters in a portion of subsurface vasculature in the body of the user and then transmit the data to a remote server, which may include a mobile device, a personal computer, the cloud, or any other remote system, for further processing. The remote server or other device could then use the transmitted data to determine a presence or status of a tumor in the body of the user. Information about such determinations could then be transmitted to the device 500 and/or could be used in some other way (e.g., could be sent to a physician's computer, could be indicated to a user via the user interface 520).

The computer readable medium 560 may further contain other data or information, such as medical and health history of a user of the device 500, that may be useful in determining whether a medical condition or some other specified condition is indicated (e.g., in determining the presence or status of a tumor in the body of a user). Further, the computer readable medium 560 may contain data corresponding to certain physiological parameter baselines, above or below which a medical condition is indicated. The baselines may be pre-stored on the computer readable medium 560, may be transmitted from a remote source, such as a remote server, or may be generated by the calculation and decision module 574 itself. The calculation and decision module 574 may include instructions for generating individual baselines for the user of the device 500 based on data collected over a period of time using the sensor 512. Baselines may also be generated by a remote server and transmitted to the device 500 via communication interface 530. The calculation and decision module 574 may also, upon determining that a medical or other emergency condition is indicated, generate one or more recommendations for the user of the device 500 based, at least in part, on consultation of a clinical protocol. Such recommendations may alternatively be generated by the remote server and transmitted to the device 500.

In some examples, detected information about an analyte in the vasculature of a user and/or and information determined therefrom about the presence or status of tumors in a user's body from a variety of different users or populations of device users may be used by physicians or clinicians in monitoring efficacy of a drug or other treatment. For example, high-density, real-time data may be collected from a population of device users who are participating in a clinical study to assess the safety and efficacy of a developmental drug or therapy. Such data may also be used on an individual level to assess a particular user's response to a drug or therapy. Based on this data, a physician or clinician may be able to tailor a drug treatment to suit an individual's needs.

In response to a determination by the calculation and decision module 574 that a medical or other specified condition is indicated (e.g., that a tumor is present in a body, that a tumor is emitting circulating tumor cells into the vasculature of the body), the alert module 576 may generate an alert via the user interface 520. The alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, seek immediate medical attention, or administer a medication (e.g., a drug to destroy or disable circulating tumor cells).

V. Example Methods

Figure 6:
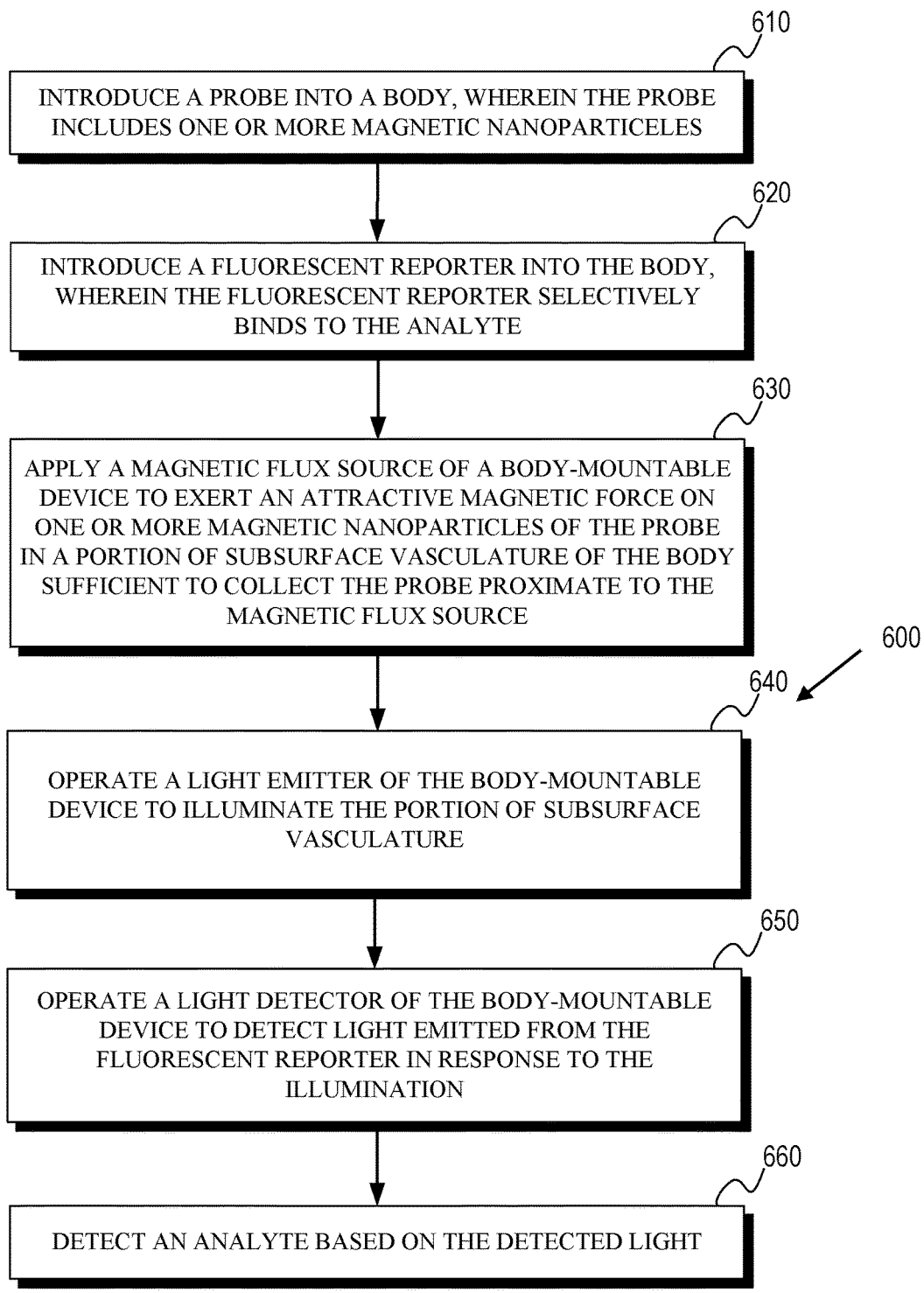
FIG. 6 is a flowchart of an example method.

FIG. 6 is a flowchart of an example method 600 for detecting an analyte in a body using a body-mountable device mounted to the body. The body-mountable device includes a magnetic flux source that is capable of exerting an attractive magnetic force to collect probes in a portion of subsurface vasculature proximate to the body-mountable device (e.g., a portion of subsurface vasculature that is beneath an external body surface to which the body-mountable device has been mounted). The probes, as described elsewhere herein, are each configured to bind to multiple instances of the analyte and each include one or more magnetic nanoparticles that can be collected in the portion of subsurface vasculature by the magnetic flux source exerting an attractive magnetic force. The body-mountable device also includes a sensor that includes a light emitter and a light detector and that is capable of detecting fluorescent reporters in the portion of subsurface vasculature proximate to the body-mountable device. The fluorescent reporters are configured to selectively bind to the analyte of interest (e.g., a particular type of EV and/or a surface protein or other external feature or element characteristic of a particular type of EVs) and include a fluorophore, a dye, a Raman dye, a fluorescent nanodiamond, a quantum dot, or some other element(s) that can be optically detected by the sensor, e.g., by illuminating the portion of subsurface vasculature using a light emitter of the sensor and detecting light responsively emitted from the fluorescent reporters using a light detector of the sensor.

The method 600 includes introducing the probe into the body (610). This could include injecting the probe into the body, e.g., using a hypodermic syringe, a transdermal patch, a catheter, an intravenous port, or some other means for introducing a substance into the vasculature of a body. A plurality of instances of the probe could be provided. Further, the probe could be introduced into the body (610) a plurality of times, e.g., to maintain a concentration of the probes in the body within a range of concentrations.

The method 600 includes introducing the fluorescent reporter into the body (620). This could include injecting the fluorescent reporter into the body, e.g., using a hypodermic syringe, a transdermal patch, a catheter, an intravenous port, or some other means for introducing a substance into the vasculature of a body. A plurality of instances of the fluorescent reporter could be provided. A timing of introduction of the fluorescent reporter (620), relative to the introduction of the probe (610) could be specified to facilitate the detection of the analyte in the body. For instance, the probe could be introduced hours, days, or weeks before introduction of the fluorescent reporter, such that the probe can circulate within the vasculature of the body during the intervening time period and collect multiple instances of the analyte.

The method 600 includes applying the magnetic flux source of the body-mountable device to exert an attractive magnetic force on one or more magnetic nanoparticles of the probe in a portion of subsurface vasculature sufficient to collect the probe proximate to the magnetic flux source (630). This could include mounting the body-mountable device to an external body surface proximate to the portion of subsurface vasculature, e.g., the magnetic flux source could include one or more permanent magnets or other magnetic elements configured to produce a magnetic flux sufficient to collect such a probe. Additionally or alternatively, the magnetic flux source could include one or more electromagnets, could include one or more permanent magnets or other magnetic elements that are able to be mechanically actuated, or could be otherwise configured to produce a controllable amount of magnetic flux, and applying the magnetic flux source to exert an attractive magnetic force (630) could include operating the magnetic flux source to produce such a controlled amount of flux. For example, a current could be applied through an electromagnet of the magnetic flux source to control a magnetic force exerted by the magnetic flux source. In some examples, elements of the magnetic flux source could be mechanically actuated to control the amount of attractive magnetic force applied to the probe in the portion of subsurface vasculature, e.g., by moving a magnetic shield or pole or by rotating one or more permanent magnets to face the external body surface.

The method 600 includes operating the light emitter of the body-mountable device to illuminate the portion of subsurface vasculature (640). This could include producing illumination at a specified wavelength, e.g., at an excitation wavelength of a fluorophore, a fluorescent defect or dopant in a nanodiamond, a quantum dot, or some other light-absorbing substance or element of the fluorescent reporter.

The method 600 additionally includes operating the light detector of the body-mountable device to detect light emitted from the fluorescent reporters in response to the illumination (650). This could include detecting an intensity, a spectrum, a color, or some other property of light reflected, refracted, fluorescently absorbed and re-emitted, scattered, or otherwise emitted by the fluorescent reporter (e.g., by a fluorophore, chromophore, Raman dye, fluorescent nanodiamond, quantum dot, or other element of the probe).

The method 600 additionally includes detecting the analyte based on the detected light (660). This could include determining an amount of the analyte that is present in the portion of subsurface vasculature based on the intensity or some other property of the detected light. Determining an amount of the analyte in the portion of subsurface vasculature could include determining a concentration of the analyte in the portion of subsurface vasculature and/or in the whole body, a number of instances of the analyte in the portion of subsurface vasculature, a mass of the analyte in the portion of subsurface vasculature, that the analyte is present in the portion of subsurface vasculature, that an amount of the analyte in the portion of subsurface vasculature is greater than some threshold amount, or making some other determination about the amount of the analyte in the portion of subsurface vasculature and/or in the body as a whole. Such determinations could be made based on a detected amount of the probe that is collected in the portion of subsurface vasculature (e.g., an amount of the probe detected by detecting a fluorophore, magnetic nanoparticle, or other detectable element(s) of the probe), a timing and/or amount of the probe and/or fluorescent reporter that is introduced into the body, binding dynamics or kinetics of the analyte to the probe and/or the fluorescent reporter, or some other information.

The method 600 could include additional steps or elements. For example, the method 600 could include determining a tumor presence or status or some other health state based on the measured amount of the analyte (e.g., based on a determined amount of a particular type of EV) in the portion of subsurface vasculature. The method 600 could additionally include providing an indication of the determined amount or other properties of the analyte using a user interface of a wearable device, a communication interface, or some other means. The method 600 could include controlling an amount of magnetic force exerted by the magnetic flux source over time. For example, the method 600 could include exerting a magnetic force during a first period of time that is insufficient to collect magnetic nanoparticle-containing probes (e.g., exerting substantially no magnetic force) such that the probes can pass by the body-mountable device to continue circulating in the vasculature and collecting additional instances of the analyte. The method 600 could also include, during a second period of time, exerting an attractive magnetic force that is sufficient to collect the probes in the portion of subsurface vasculature such that the analyte can be detected using the sensor (e.g., by detecting the fluorescent reporter bound to instances of the analyte that are bound to the probes). The method 600 could include additional or alternative steps.

VI. Conclusion

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

Where example embodiments involve information related to a person or a device of a person, such embodiments may include privacy controls. Such privacy controls may include, at least, anonymization of device identifiers, transparency and user controls, including functionality that would enable users to modify or delete information relating to the user's use of a product.

Further, in situations wherein embodiments discussed herein collect personal information about users, or make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

What is claimed is:

1. A body-mountable device comprising:
a magnetic flux source that, when mounted to an external body surface, can exert an attractive magnetic force on probes disposed in a portion of subsurface vasculature, wherein the exerted magnetic force is sufficient to collect the probes within the portion of subsurface vasculature, and wherein each probe comprises one or more magnetic nanoparticles and includes multiple binding sites that enable the probe to bind to multiple instances of an analyte such that an instance of the analyte that is bound to the probe can further bind to a fluorescent reporter that is separate from the probe;
a sensor comprising a light emitter and a light detector; and
a controller operably coupled to the sensor, wherein the controller comprises a computing device programmed to perform controller operations comprising:
operating the light emitter, during a detection period, to illuminate the probes collected within the portion of subsurface vasculature, wherein the detection period is a specified period of time relative to at least one of a timing of introduction of the probes into a body to which the device is mounted, a timing of introduction of the fluorescent reporter into the body to which the device is mounted, or a timing of mounting the device to the body;
operating the light detector, during the detection period, to detect light emitted from fluorescent reporters bound to instances of the analyte that are bound to the collected probes in response to the illumination; and
detecting the analyte based on the detected light.

2. The body-mountable device of claim 1, wherein the analyte is related to a presence or status of a tumor in the body.

3. The body-mountable device of claim 1, wherein the analyte comprises a particular type of extracellular vesicle that is produced by a tumor.

4. The body-mountable device of claim 3, wherein each probe is configured to selectively bind to multiple different types of extracellular vesicles including the particular type of extracellular vesicle.

5. The body-mountable device of claim 4, wherein each probe includes at least one of an anti-CD81 antibody, an anti-CD63 antibody, an anti-CD9 antibody, or an anti-ALIX antibody.

6. The body-mountable device of claim 1, wherein each probe selectively binds to the analyte.

7. The body-mountable device of claim 6, wherein the probes and the fluorescent reporters comprise respective different binding agents that selectively bind to the analyte.

8. The body-mountable device of claim 1, wherein the controller is operably coupled to the magnetic flux source, and wherein the controller operations further comprise:
operating the magnetic flux source, during a first period of time, to exert a first magnetic force, wherein the first magnetic force is insufficient to collect the probes proximate the magnetic flux source; and
operating the magnetic flux source, during a second period of time, to exert a second attractive magnetic force that that is sufficient to collect the probes proximate the magnetic flux source.

9. The body-mountable device of claim 1, wherein the body-mountable device comprises a wearable device.

10. A method comprising:
introducing probes into a body, wherein each probe comprises one or more magnetic nanoparticles and includes multiple binding sites that enable the probe to bind to multiple instances of an analyte such that an instance of the analyte that is bound to the probe can further bind to a fluorescent reporter that is separate from the probe;
introducing the fluorescent reporter into the body, wherein the fluorescent reporter selectively binds to the analyte;
applying a magnetic flux to the body to exert an attractive magnetic force the probes in a portion of subsurface vasculature of the body, wherein the exerted magnetic force is sufficient to collect the probes within the portion of subsurface vasculature;
illuminating the probes collected within the portion of subsurface vasculature;
detecting light emitted from fluorescent reporters bound to instances of the analyte that are bound to the collected probes in response to the illumination; and
detecting the analyte based on the detected light.

11. The method of claim 10, wherein the analyte is related to a presence or status of a tumor in the body.

12. The method of claim 11, further comprising:
providing an indication of a presence or status of the tumor in response to detecting the analyte.

13. The method of claim 10, wherein the analyte comprises a particular type of extracellular vesicle that is produced by a tumor.

14. The method of claim 13, wherein each probe is configured to selectively bind to multiple different types of extracellular vesicles including the particular type of extracellular vesicle.

15. The method of claim 14, wherein each probe includes at least one of an anti-CD81 antibody, an anti-CD63 antibody, an anti-CD9 antibody, or an anti-ALIX antibody.

16. The method of claim 10, wherein each probe selectively binds to the analyte.

17. The method of claim 16, wherein the probes and the fluorescent reporters comprise respective different binding agents that selectively bind to the analyte.

18. The method of claim 10, wherein the magnetic flux is applied by a body-mountable device that comprises:
a magnetic flux source that is operable to produce the applied magnetic flux; and
a sensor comprising a light emitter and a light detector, wherein illuminating the probes collected within the portion of subsurface vasculature comprises operating the light emitter to produce the illumination, and wherein detecting light emitted from fluorescent reporters in response to the illumination comprises operating the light detector to detect the emitted light.

19. The method of claim 18, wherein the method further comprises:
operating the magnetic flux source, during a first period of time, to exert a first magnetic force, wherein the first magnetic force is insufficient to collect the probes in the portion of subsurface vasculature proximate the magnetic flux source; and
operating the magnetic flux source, during a second period of time, to exert a second attractive magnetic force that that is sufficient to collect the probes in the portion of subsurface vasculature proximate the magnetic flux source.

* * * * *